United States Patent
Bolduc et al.

(10) Patent No.: US 11,882,826 B2
(45) Date of Patent: *Jan. 30, 2024

(54) PERFORMIC ACID BIOFILM PREVENTION FOR INDUSTRIAL $CO_2$ SCRUBBERS

(71) Applicant: ECOLAB USA INC., Saint Paul, MN (US)

(72) Inventors: John Bolduc, Saint Paul, MN (US); Chris Nagel, Saint Paul, MN (US); Junzhong Li, Saint Paul, MN (US); Catherine Hanson, Saint Paul, MN (US); Peter Fernholz, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 23 days.

This patent is subject to a terminal disclaimer.

(21) Appl. No.: 17/646,239

(22) Filed: Dec. 28, 2021

(65) Prior Publication Data

US 2022/0117226 A1    Apr. 21, 2022

Related U.S. Application Data

(63) Continuation of application No. 16/362,885, filed on Mar. 25, 2019, now Pat. No. 11,241,009, which is a
(Continued)

(51) Int. Cl.
*B08B 17/00* (2006.01)
*A61L 2/00* (2006.01)
(Continued)

(52) U.S. Cl.
CPC ............ *A01N 37/16* (2013.01); *A01N 25/02* (2013.01); *A01N 37/02* (2013.01); *A01N 59/00* (2013.01);
(Continued)

(58) Field of Classification Search
CPC ........ A61L 2/0082; A61L 2/0088; A61L 2/16; A01N 37/34; A01N 25/04; A61M 35/003
(Continued)

(56) References Cited

U.S. PATENT DOCUMENTS 5,616,335 A    4/1997    Nicolle et al.
6,139,756 A    10/2000   Fuchs et al.
(Continued)

FOREIGN PATENT DOCUMENTS

AU    2007311532 A1    4/2008
CA       2131664 A1    3/1995
(Continued)

OTHER PUBLICATIONS

European Patent Office, "Extended European Search Report", in connection with PCT/US2016/067139 filed Dec. 16, 2016, 8 pages, dated Jun. 28, 2019.
(Continued)

*Primary Examiner* — Monzer R Chorbaji
(74) *Attorney, Agent, or Firm* — McKee, Voorhees & Sease, PLC

(57) ABSTRACT

Peroxyformic acid compositions for removal of biofilm growth and other contaminants and impurities from industrial processing hard surfaces are disclosed. In particular, peroxyformic acid compositions may be dosed on site and/or generated in situ for the reduction and prevention of biofilms on the hard surfaces. Methods of employing the peroxyformic acid compositions for removal of biofilm growth and other impurities such as aldehydes and alcohols from industrial $CO_2$ effluent are also disclosed which beneficially provide ambient biofilm control and break down more rapidly than other peracids, allowing for extended runs
(Continued)

between CIP cleaning, including a reduction and/or elimination of cleaning of the scrubbers and other industrial surfaces.

18 Claims, 7 Drawing Sheets

Related U.S. Application Data continuation of application No. 15/487,641, filed on Apr. 14, 2017, now Pat. No. 10,278,392.

(60) Provisional application No. 62/323,024, filed on Apr. 15, 2016.

(51) Int. Cl.
*A61L 9/00* (2006.01)
*B08B 7/00* (2006.01)
*B08B 9/00* (2006.01)
*A01N 37/16* (2006.01)
*A01N 37/02* (2006.01)
*A01N 59/00* (2006.01)
*A61L 2/18* (2006.01)
*A01N 25/02* (2006.01)

(52) U.S. Cl.
CPC .............. *A61L 2/18* (2013.01); *A61L 2/186* (2013.01); *A61L 2202/11* (2013.01); *A61L 2202/17* (2013.01)

(58) Field of Classification Search
USPC ........... 422/6, 28, 32; 134/6, 22.1, 22.11, 26
See application file for complete search history.

(56) References Cited

U.S. PATENT DOCUMENTS

| | | | |
|---|---|---|---|
| 6,211,237 B1 | 4/2001 | Huss et al. | |
| 6,254,801 B1 | 7/2001 | Reinold et al. | |
| 6,284,719 B1 | 9/2001 | Simms | |
| 6,468,472 B1 | 10/2002 | Yu et al. | |
| 7,638,067 B2 | 12/2009 | Hilgren et al. | |
| 7,915,445 B2 | 3/2011 | Maatta et al. | |
| 8,802,061 B2 | 8/2014 | Tichy et al. | |
| 8,828,910 B2 | 9/2014 | Aksela et al. | |
| 8,877,354 B2 | 11/2014 | Horiuchi et al. | |
| 9,044,403 B2 | 6/2015 | Schultz | |
| 9,192,909 B2 | 11/2015 | Kraus et al. | |
| 9,617,170 B2 | 4/2017 | Karpova et al. | |
| 10,278,392 B2 * | 5/2019 | Bolduc .............. A01N 25/02 | |
| 2002/0177732 A1 | 11/2002 | Pohjanvesi et al. | |
| 2004/0143133 A1 | 7/2004 | Smith et al. | |
| 2005/0072743 A1 | 4/2005 | Schneider et al. | |
| 2006/0177518 A1 | 8/2006 | Stevenson et al. | |
| 2007/0023363 A1 | 2/2007 | Daines et al. | |
| 2007/0056904 A1 | 3/2007 | Hogt et al. | |
| 2007/0249712 A1 | 10/2007 | Dee et al. | |
| 2008/0095677 A1 | 4/2008 | McSherry et al. | |
| 2009/0200234 A1 | 8/2009 | Schacht et al. | |
| 2009/0221704 A1 | 9/2009 | Aksela et al. | |
| 2009/0320214 A1 | 12/2009 | Shamayeli et al. | |
| 2010/0084340 A1 | 4/2010 | Monsrud et al. | |
| 2011/0094044 A1 | 4/2011 | Shamayeli et al. | |
| 2012/0228221 A1 | 9/2012 | Kakigami et al. | |
| 2013/0065958 A1 | 3/2013 | Dunn | |
| 2013/0079733 A1 * | 3/2013 | Burt ................. B05B 17/0607 239/102.1 | |
| 2013/0203849 A1 | 8/2013 | Ben Yehuda | |
| 2014/0039050 A1 | 2/2014 | da Costa et al. | |
| 2014/0097144 A1 | 4/2014 | Li et al. | |
| 2014/0124461 A1 | 5/2014 | Buisson et al. | |
| 2014/0274857 A1 | 9/2014 | Schacht et al. | |
| 2014/0367334 A1 | 12/2014 | Salonen et al. | |
| 2015/0018319 A1 | 1/2015 | Larson et al. | |
| 2015/0056679 A1 | 2/2015 | Patten et al. | |
| 2015/0183673 A1 | 7/2015 | Musale et al. | |
| 2015/0240328 A1 | 8/2015 | Urbani | |
| 2015/0351383 A1 | 12/2015 | Kolari et al. | |
| 2015/0351389 A1 * | 12/2015 | Kolari .................... A01N 37/34 514/528 |
| 2016/0068417 A1 | 3/2016 | Buschmann | |

FOREIGN PATENT DOCUMENTS

| | | | |
|---|---|---|---|
| CA | 2300807 A1 | 9/2000 | |
| CA | 2475361 A1 | 8/2003 | |
| CA | 3009259 A1 | 6/2017 | |
| CN | 101054779 B | 5/2012 | |
| CN | 102876287 B | 6/2014 | |
| CN | 104206413 A | 12/2014 | |
| CN | 107925112 A | 4/2018 | |
| DE | 3134050 A1 | 3/1983 | |
| DE | 3504394 A1 | 9/1985 | |
| EP | 0231632 A2 | 8/1987 | |
| EP | 0231632 A3 | 8/1987 | |
| EP | 1022946 B1 | 8/2000 | |
| EP | 1172335 A1 | 1/2002 | |
| EP | 1247802 A1 | 10/2002 | |
| EP | 1125497 A2 | 6/2003 | |
| EP | 1244842 B1 | 1/2004 | |
| EP | 1131016 B1 | 2/2005 | |
| EP | 2609990 A1 | 7/2013 | |
| EP | 2653448 B1 | 2/2018 | |
| EP | 3169844 B1 | 12/2018 | |
| FI | 113056 B | 2/1999 | |
| FI | 126082 B | 7/2014 | |
| JP | 60175504 A | 9/1985 | |
| JP | 2000117069 A | 4/2000 | |
| JP | 2005154551 A | 6/2005 | |
| JP | 2008100161 A | 5/2008 | |
| JP | 4533618 B2 | 9/2010 | |
| WO | 9420424 A1 | 9/1994 | |
| WO | 9517241 A1 | 6/1995 | |
| WO | 9623858 A1 | 8/1996 | |
| WO | 9719594 A1 | 6/1997 | |
| WO | 9856988 A1 | 12/1998 | |
| WO | 9946234 A1 | 9/1999 | |
| WO | 2000045639 A1 | 8/2000 | |
| WO | 0170030 A2 | 9/2001 | |
| WO | 0170030 A3 | 9/2001 | |
| WO | 03092919 A1 | 11/2003 | |
| WO | 2004012510 A1 | 2/2004 | |
| WO | 2005005028 A1 | 1/2005 | |
| WO | 2007031596 A2 | 3/2007 | |
| WO | 2007031596 A3 | 3/2007 | |
| WO | 2007070609 A2 | 6/2007 | |
| WO | 2008056025 A3 | 5/2008 | |
| WO | 2008088873 A1 | 7/2008 | |
| WO | 2008120509 A1 | 10/2008 | |
| WO | 2011006019 A2 | 1/2011 | |
| WO | 2012025943 A1 | 3/2012 | |
| WO | 2012025943 A4 | 3/2012 | |
| WO | 2012113042 A1 | 8/2012 | |
| WO | 2012177366 A2 | 12/2012 | |
| WO | 2012177366 A3 | 12/2012 | |
| WO | 2013051013 A2 | 4/2013 | |
| WO | 2013098478 A2 | 7/2013 | |
| WO | 2013098479 A1 | 7/2013 | |
| WO | 20130175062 A1 | 11/2013 | |
| WO | 2013184605 A1 | 12/2013 | |
| WO | 2014062487 A1 | 4/2014 | |
| WO | 2014154946 A1 | 10/2014 | |
| WO | 2016100694 A1 | 6/2016 | |
| WO | 2016100700 A1 | 6/2016 | |
| WO | 2017040920 A1 | 3/2017 | |
| WO | 2017106623 A1 | 6/2017 | |
| WO | 2017181005 A1 | 10/2017 | |
| WO | 2017194842 A1 | 11/2017 | |

(56) References Cited

FOREIGN PATENT DOCUMENTS

| WO | 2018091784 A1 | 5/2018 |
|---|---|---|
| WO | 2018111341 A1 | 6/2018 |

OTHER PUBLICATIONS

European Patent Office, "Extended European Search Report", in connection with PCT/US2017/027622 filed Apr. 14, 2017, 11 pages, dated Aug. 16, 2019.

Ecolab USA Inc., PCT/US2017/037467 filed Jun. 14, 2017, "Notification of Transmittal of The International Search Report and The Written Opinion of The International Searching Authority, or The Declaration", dated Sep. 5, 2017.

Ecolab USA Inc., PCT/US2016/067139 filed Dec. 16, 2016, "The International Search Report and The Written Opinion of the International Searching Authority, or the Declaration", dated Jun. 1, 2017.

Ecolab USA, Inc., PCT/US2017/027622 filed Apr. 15, 2016, "International Search Report", dated Jul. 27, 2016.

Johnson, Greg, et al. "Kinetics of Mineral Scale Membrane Fouling" Technical Article, 14 pages, accessed from www.vsep.com as of Dec. 1, 2016.

Vance, Frederick W., et al. "New Solution for Controlling of Organic and BioFouling in High Pressure Membrane Applications" AMTA/AWWA Membrane Technology Conference & Exposition 2013, San Antonio, Texas, Feb. 25-28, 2013, vol. 2 of 2, 14 pages Feb. 25, 2013.

DeJong, Robert L., "Atmospheric Corrosion Problems in Secondary Fibre Plants", Enzyme Microb. Technol. (Jul. 1979) vol. 1, p. 205-209 Jul. 1979.

Littlejohn, et al., "Removal of NOx and SO2 from Flue Gas by Peracid Solutions", Ind. Eng. Chem. Res. (1990) 29, pp. 1420-1424. 1990.

* cited by examiner

PERFORMIC ACID BIOFILM PREVENTION FOR INDUSTRIAL $CO_2$ SCRUBBERS

CROSS-REFERENCE TO RELATED APPLICATIONS

This is a Continuation Application of U.S. Ser. No. 16/362,885, filed Mar. 25, 2019, which is a Continuation Application of U.S. Ser. No. 15/487,641, filed Apr. 14, 2017, now U.S. Pat. No. 10,278,392, issued May 7, 2019, which claims priority under 35 U.S.C. § 119 to provisional application Ser. No. 62/323,024, filed Apr. 15, 2016, titled "Performic Acid Biofilm Prevention For Industrial $CO_2$ Scrubbers," which is herein incorporated by reference in its entirety.

FIELD OF THE INVENTION

The invention relates to use of peroxyformic acid compositions for removal of biofilm growth and other impurities such as aldehydes and alcohols from industrial $CO_2$ effluent. Accordingly, the present invention relates to the field of biofilm control and CIP cleaning of scrubbers and other industrial surfaces. In particular, peroxyformic acid compositions can be generated in situ or on site or provided in a pre-formed composition for the reduction, removal and/or kill of biofilms and the mitigation of other impurities on such hard surfaces. The compositions according to the invention beneficially provide ambient biofilm control and break down more rapidly than other peracids, allowing for extended runs between CIP cleaning, including a reduction and/or elimination of cleaning of the scrubbers and other industrial surfaces.

BACKGROUND OF THE INVENTION

Industrial processing surfaces, including scrubbers, are conventionally treated using clean-in-place (CIP) methods to provide flushing, rinsing, pretreatment, cleaning, disinfecting, sanitizing and preserving, in order to prevent fouling during processing. Fouling components and deposits can include inorganic salts, particulates, microbials and organics. Fouling manifests itself as a decline in performance and/or quality of the finished goods. Fouling can also include biofilm growth along with other impurities within industrial processing systems, such as $CO_2$ scrubbers employed in ethanol and other fermentation systems, having detrimental results. As a result, CIP processes are utilized to circulate cleaning agents over and through the industrial processing surfaces to wet, penetrate, dissolve and/or rinse away foreign materials. Various parameters that can be manipulated for cleaning typically include time, temperature, mechanical energy, chemical composition, chemical concentration, soil type, water type, and hydraulic design. Conventional cleaning techniques include the use of high heat and/or extreme pH, i.e., very high alkalinity use solutions, or very low pH acidic use solutions. However, many surfaces cannot tolerate such conditions.

In an exemplary industrial processing, $CO_2$ scrubbers are often used to remove impurities such as aldehydes and alcohols from the industrial effluent by spraying water through a column packed with porous spheres of HDPE plastic to improve surface contact. However, over time, biofilms form inside the scrubbers, causing plugging, fouling, reduction of optimal flow, and potential contamination of the upstream process in cases where ethanol (EtOH) is reclaimed back into the process that has been carried out with the $CO_2$. Such biofilm growth and impurities, such as aldehydes and alcohols, need to be removed from industrial surfaces to prevent severe decline in production and operation of the systems which can also negatively impact the quality of finished goods, and often premature replacement of such industrial processing systems.

Among various biocides known, peroxycarboxylic acids are increasingly used as antimicrobials and bleaching agents in many applications, owing to their high efficacy against a broad spectrum of microorganisms, color safe property, low residues and nontoxic nature of their decomposition products. Peracetic acid is the most commonly used peroxycarboxylic acid and has been shown to be a good biocide, but only at relatively high concentrations (generally greater than 80 part per million). Similarly, peroxyfatty acids have also been shown to be biocidal, but only at high concentrations (greater than 200 ppm), such as in the composition disclosed in European Patent Application No. 233,731. In contrast, peroxyformic acid has an advantageous degree and range of microcidal properties compared to other peroxycarboxylic acids, such as peracetic and perproprionic acids, as disclosed by V. Merka et al in J. Hyg. Epidem. Microbiol. Immunol, 1965 (IX) 220, as well as in European Patent Application No. 863,098,96.

Although various agents preventing microbial growth, such as oxidizers and biocides, are known for cleaning industrial processing surfaces, including CIP cleaning techniques, there is still a need for an improved method for the prevention of microbial growth and biofilm formation.

Biofilms are biological conglomerates that contain pathogens, such as bacteria and other microorganisms, embedded in a matrix of exopolymers and macromolecules. In addition to bacteria, other microorganisms are commonly found in biofilm, including fungi, molds, algae, protozoa, archaea and mixtures of these microorganisms. Biofilms form as a result of microorganisms establishing on a surface and producing a protective extracellular polymeric matrix. Most often biofilm form on surfaces in contact with water, providing a hydrated matrix of polysaccharides to provide structural protection from biocides, making biofilm more difficult to kill than other pathogens.

Microbial infection and the formation of biofilm present significant complications in numerous industries. Although biofilm are known to exist in a wide-variety of environmental conditions, since biofilm most often form on surfaces exposed to bacteria and water, industries such as food processing are commonly affected by biofilm. For example, the organism *Listeria monocytogenes* thrives in cool, damp environments, such as floor drains, plumbing and other surfaces of food processing facilities. This provides a potential point of contamination for a processing plant environment and food products produced therein. However, biofilm can also develop on inert surfaces of everyday household items. Exposure to such microorganisms through skin-surface contact may result in infections and compromise the public's health. Therefore, controlling the formation of biofilm is desirable to decrease exposure to infectious microorganisms.

Biofilm growth and removal depends on several factors, including the surface composition and chemical composition of the surrounding environment. Several biofilm removal methods are utilized, including physical, chemical and biological removal. Means of physically removing biofilm include the use of magnetic fields, ultra sound, high and low electrical fields and abrasive techniques. Physical removal techniques are often combined with chemical or biological methods, such as biocides or antimicrobial agents.

A number of technologies have been developed that treat surfaces with organic or inorganic materials to interfere with biofilm development, such as preventing microbial attack and degradation. For example, coating a surface with or incorporating a composition into a surface substrate to create a surface wherein microorganisms do not adhere or colonize. U.S. Pat. No. 9,072,292. However, such technologies have not effectively eliminated biofilm formation and growth. Therefore, the contamination of surfaces with biofilm remains a problem.

In light of the foregoing, there remains a demand for compositions and methods for reducing and removing biofilm.

Accordingly, it is an objective of the claimed invention to provide peroxyformic acid compositions, including those which can be generated in situ for the prevention and removal of microbial growth and biofouling from industrial processing surfaces, including $CO_2$ scrubbers.

Other objects, advantages and features of the present invention will become apparent from the following specification taken in conjunction with the accompanying drawings.

BRIEF SUMMARY OF THE INVENTION

The invention provides a peroxycarboxylic acid composition comprising peroxyformic acid, which may be generated in situ or on site, for use to remove and/or reduce biofilm growth and other contaminants and impurities from industrial processing surfaces, including $CO_2$ scrubbers. Examples of contaminants include for example, particulate matter, organic and inorganic contaminants, oils, process contaminants, microorganisms, and so forth. Suspended matter in the industrial processes, and waters associated therewith, provide the microorganisms with readily available nourishment for sustaining life and reproduction. It is well established that the presence of inorganic, organic, and microbiological deposits have a detrimental impact on the operational parameters of an industrial processing system, resulting in reduced efficiency and increased operating cost.

It is an advantage of the present invention that the cleaning compositions are biodegradable, decompose into non-hazardous products which therefore leave no toxic traces on the treated surfaces (due to rapid degradation into water, carbon dioxide and formic acid which are recognized as GRAS) and therefore do not negatively interfere with the fermentation or other products generated within such industrial processing surfaces. Moreover, the peroxyformic acid composition is suitable for generation in situ or on site of a point of use, allowing a user to promptly apply the composition to a surface in need of treatment.

In an aspect, methods of the invention are directed to methods of removing biofilm and/or other impurities from industrial $CO_2$ scrubbers. In a further aspect, the methods of the invention are directed to intermittent treatment of process water streams feeding the industrial processing surfaces, such as scrubbers, with the peroxyformic acid compositions. Beneficially, the peroxyformic acid compositions provide ambient biofilm control and removal of other microbial and/or other impurities and contaminants, while breaking down rapidly in comparison to other peracids and peracid compositions.

In an aspect, methods of the invention are directed to methods of cleaning industrial processing surfaces, such as scrubbers, to provide extended periods of time for processing (or runs) between conventional clean-in-place (CIP) cleaning methods. In a further aspect, methods of the invention are directed to methods of cleaning the industrial processing surfaces, such as scrubbers, to reduce and/or eliminate the cleaning of such surfaces.

In a further embodiment, the present invention discloses onsite generated peroxycarboxylic acid compositions comprising performic acid that efficiently kill and removal biofilms and other soils, contaminants and impurities without damaging or negatively interfering with the treated surfaces.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
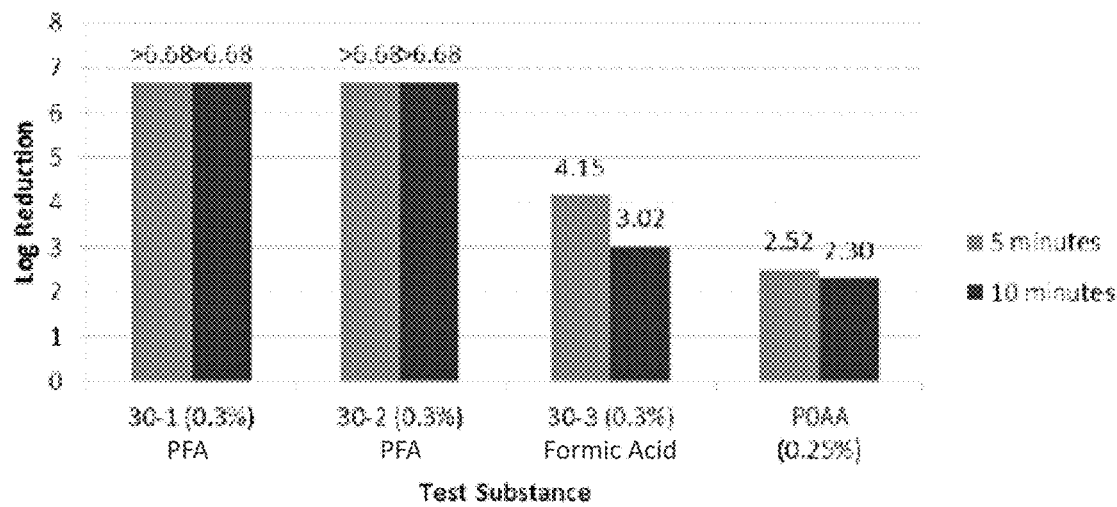
FIG. 1 is a graphical representation showing the average log reduction of *P. aeruginosa* biofilm after exposure to the peroxyformic acid formulations according to an embodiment of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENT

The present invention relates to peroxycarboxylic acid compositions comprising peroxyformic acid, including those which can be generated in situ or on site, for use to reduce and/or prevent biofilm growth and other contaminants and impurities from treated surfaces. The embodiments of this invention are not limited to particular peroxyformic acid compositions, which can vary and are understood by skilled artisans based on the disclosure herein of the present invention. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The term "biofilm," as used herein, means an extracellular matrix in which a population of microorganisms are dispersed and/or form colonies. Biofilms are understood to be typically made of polysaccharides and other macromolecules, often referred to as exopolysaccharides, that are concentrated at an interface (usually solid/liquid) and act as a binding agent that surrounds such populations of microorganisms. Biofilms are further understood to include complex associations of cells, extracellular products and detritus (or non-living particulate organic material) that are trapped within the biofilm or released from cells within the biofilm. The term biofilm, as used herein, further refers to the ASTM definition of biofilm as an accumulation of bacterial cells immobilized on a substratum and embedded in an organic polymer matrix of microbial origin. Biofilms are understood to be a dynamic, self-organized accumulation of microorganisms and microbial and environmental by-products that is determined by the environment in which it lives. According to the invention, the phrases "biofilm remediation," "removing biofilm," "reducing biofilm" and like phrases, shall mean the use of the chemical biocide according to the invention which causes a reduction in the rate or extent of biofilm growth, removal of existing biofilm or portions of biofilm on surfaces and/or eradication of existing biofilm on a treated surface. According to the invention, the biocidal compositions disclosed herein physically remove and kill biofilm.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

The term "Distillers Dried Grains" (DDG), as used herein refers generally to coproducts of ethanol production by fermentation which can comprise dried residual grain solids, which can be animal feed grade. "Distillers Dried Grains with Solubles" (DDGS) refers to coproducts of ethanol production by fermentation which can comprise dried residual grain solids with solubles content, such as process syrup or other solubles, and which can be animal feed grade. "Wet Distillers Grains" (WDG) refers to coproducts of ethanol production by fermentation which can comprise residual grain solids prior to drying, which can contain at least a portion of process syrup, and which can be animal feed grade.

As it pertains to this disclosure, "fouling" and "contamination" refer to the presence or the deposition of any extraneous or undesirable organic or inorganic material in a water-containing industrial process or onto one or more surfaces within the water-containing industrial process. "Microbial fouling" refers to the presence or deposition of any extraneous or undesirable microbiological organism in a water-containing industrial process.

The term "generally recognized as safe" or "GRAS," as used herein refers to components classified by the Food and Drug Administration as safe for direct human food consumption or as an ingredient based upon current good manufacturing practice conditions of use, as defined for example in 21 C.F.R. Chapter 1, § 170.38 and/or 570.38.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 3 log reduction and more preferably a 5-log order reduction. These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "soil" or "stain" refers to a non-polar oily substance which may or may not contain particulate matter such as mineral clays, sand, natural mineral matter, carbon black, graphite, kaolin, environmental dust, etc.

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition The term "substantially similar cleaning performance" refers generally to achievement by a substitute cleaning product or substitute cleaning system of generally the same degree (or at least not a significantly lesser degree) of cleanliness or with generally the same expenditure (or at least not a significantly lesser expenditure) of effort, or both.

As used herein, the term "sulfoperoxycarboxylic acid," "sulfonated peracid," or "sulfonated peroxycarboxylic acid" refers to the peroxycarboxylic acid form of a sulfonated carboxylic acid. In some embodiments, the sulfonated peracids of the present invention are mid-chain sulfonated peracids. As used herein, the term "mid-chain sulfonated peracid" refers to a peracid compound that includes a sulfonate group attached to a carbon that is at least one carbon (e.g., the three position or further) from the carbon of the percarboxylic acid group in the carbon backbone of the percarboxylic acid chain, wherein the at least one carbon is not in the terminal position. As used herein, the term "terminal position," refers to the carbon on the carbon backbone chain of a percarboxylic acid that is furthest from the percarboxyl group.

The term "threshold agent" refers to a compound that inhibits crystallization of water hardness ions from solution, but that need not form a specific complex with the water hardness ion. Threshold agents include but are not limited to a polyacrylate, a polymethacrylate, an olefin/maleic copolymer, and the like.

As used herein, the term "waters" includes cooling tower waters, food process or transport waters. Cooling tower waters include water being used in scrubbers, cooling towers and the like, including where water is performing the function of collecting impurities, capturing product and/or cooling the equipment. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, systems, apparatuses, and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The methods and peroxyformic acid compositions according to the embodiments of the invention present a significant improvement in the prior art and represent a significant change for industries in need of cleaning and sanitizing products for biofilm. The biofilm remediation methods and compositions according to the invention obviate the need for numerous biofilm-reducing agents that are individually and/or in combination unable to completely remove and/or kill biofilm. The biofilm remediation compositions according to the invention provide a superior biocidal product, resulting in improved kill rates of biofilm over known methods of chemical and biological removal or reduction. This is a beneficial result of the biofilm remediation compositions according to the invention having a "kill mechanism" capable of penetrating all layers of a biofilm composition and reaching the substrate surface. These and other benefits of the biofilm remediation methods and compositions according to the invention will be readily apparent based on the description contained here, providing improved compositions and methods for treating ubiquitous biofilm.

Various biofilm-reducing agents are known to provide some beneficial effects in biofilm reduction and/or prevention. For example, chelating agents such as EDTA and EGTA, chlorine, iodine and hydrogen peroxide have previously been used as biofilm-reducing agents. Chelating agents destabilize the outer cell membrane of the biofilm. Chlorine, iodine, and hydrogen peroxide remove biofilm by depolymerizing the matrix. Further, biofilm-reducing agents may include antimicrobial proteins, such as nisin, which may be produced by *Lactococcus lactus*. Biocides or antimicrobial agents are also used as biofilm-reducing agents. Examples of biocides or antimicrobial agents that are effective include: iodophores; phenols including halo- and nitro-phenols and substituted bisphenols such as 4-hexylresorcinol, 2-benzyl-4-chlorophenol and 2,4,4'-trichloro-2'-hydroxydiphenyl ether; quaternary ammonium compounds and other cationic compounds; cationic surfactants such as alkyl and benzyl quaternary compounds like N-alkyl ($C_{12}$-$C_{18}$) dimethylbenzyl ammonium chloride monohydrate, dimethyl didecyl ammonium chloride, and N-alkyl and ($C_{12}$-$C_{14}$) dimethyl I-napthylmethyl ammonium chloride; organic and inorganic acids and its esters and salts such as dehydroacetic acid, methyl p-hydroxy benzoic acid; aldehydes such as glutaraldehyde; antimicrobial dyes such as is acridines, triphenylmethane dyes and quinones and halogens.

However, as described according to the invention, the peroxyformic acid compositions and methods described herein provide enhanced antimicrobial "-cidal" mechanisms that are superior over prior biofilm-reducing agents. According to a preferred embodiment, the biofilm remediation composition and methods provide up to a 5-log order reduction in the population of microorganisms and pathogens in biofilm, compared to the optimal 3-log order reduction observed with use of the biofilm-reducing agents described above. The beneficial results of the biofilm remediation composition according to the invention result from the composition's penetration of all layers of a biofilm to the substrate surface, providing a complete kill of the microorganisms housed in such biofilm.

Methods of Cleaning Industrial Processing Surfaces

The present invention comprises peroxyformic acid compositions which can be used as a cleaning composition, namely an antimicrobial cleaning composition, a booster or as part of an alkaline, acid and/or enzymatic cleaning composition, and methods of use of the same in a periodic CIP application. In an exemplary embodiment, the antimicrobial cleaning compositions or cleaning compositions are particularly suitable for use in scrubbers and cooling towers. As referred to herein, the removing of microorganisms, biofilm, contaminants and other impurities refers to the reduction in microorganisms, biofilm, contaminants and other impurities on a hard surface within an industrial processing system, the disbursement of microorganisms, biofilm, contaminants and other impurities from such surfaces, and/or the inactivating of microorganisms, biofilm, contaminants and other impurities from such surfaces.

In an aspect, the peroxyformic acid compositions are applied to or contact a hard surface, such as a CO2 scrubber as may be found in fermentation systems, such as ethanol and/or breweries, in need of removing microbial growth and biofilm. In a further aspect, the peroxyformic acid compositions are applied to or contact a hard surface, such as a cooling tower, in need of removing microbial growth and biofilm. In a still further aspect, the peroxyformic acid compositions are applied to or contact a hard surface that has ambient water flow over a substrate (e.g. prone to microbial fouling) in need of removing microbial growth and biofilm.

The hard surfaces that can be treated according to the invention include those designed for periodic cleaning, such as those employed in ethanol and other fermentation applications, cooling towers, scrubbers, drains, sumps, floors, and the like. Exemplary industries that utilize such systems include the food industry, the beverage industry, the biotechnology industry, the pharmaceutical industry, the chemical industry, the water purification industry, and the ethanol fermentation industry. In an aspect, surfaces particularly suited for treatment according to the invention include aqueous cooling systems and scrubbers. Additional suitable surfaces for treatment are disclosed in U.S. Patent Publication Nos. 2014/0263086, 2014/0271418 which are incorporated by reference in its entirety.

In a preferred aspect, the hard surface is a scrubber and/or cooling tower, tower packing materials contained in the scrubber and/or cooling tower, drain, sump, or floor. In certain aspects, the tower and/or media contained therein (e.g. packing materials) are contacted with the peroxyformic acid compositions according to the invention. As one skilled in the art will ascertain various towers for industrial processing are packed with material (such as in the $CO_2$ column) and the ongoing flow through thereof water and other chemistry can lead to high microbial counts and therefore, the surfaces are in need of treatment according to the invention.

Figure 7:
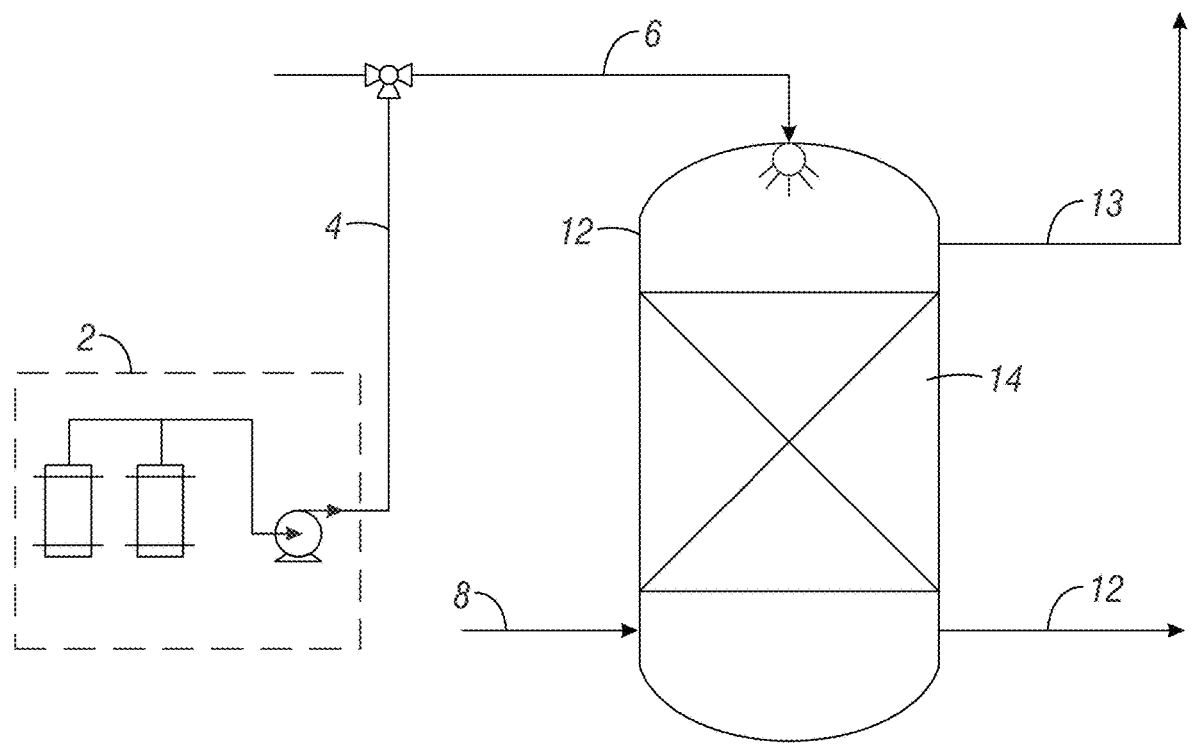
FIG. 7 shows a process diagram depicting an embodiment of the invention employing an onsite generated peroxyformic acid for treating a CO2 industrial scrubber tower.

In a depicted embodiment, as shown in FIG. 7 providing a process diagram depicting an embodiment of the invention a $CO_2$ industrial scrubber tower 12 (including a tower containing various packing material 14) can be dosed with a peroxyformic acid composition 4 (including composition generated onsite from a generator 2), wherein the composition can optionally be diluted with water 6. The exemplary depicted system is a $CO_2$ tower, where $CO_2$ is scrubbed going into the tower 8, and a process water effluent from the tower 12, along with any exhaust gas 13 are the outputs of the system.

In other aspects, additional industrial processing surfaces can benefit from the treatment with the peroxyformic acid. For example, the treatment compositions and methods described herein are suitable for various once-through, open loop, or closed loop recirculating industrial systems. Other aqueous systems include, but are not limited to, systems used in petroleum production and oil recovery (e.g., well casing, transport pipelines, etc.) and refining, geothermal wells, and other oil field applications; boilers and boiler water systems; systems used in power generation, mineral process waters including mineral washing, flotation and benefaction; paper mill digesters, washers, bleach plants, white water systems and mill water systems; black liquor evaporators in the pulp industry; gas scrubbers and air washers; continuous casting processes in the metallurgical industry; air conditioning and refrigeration systems; building fire protection heating water, such as pasteurization water; water reclamation and purification systems; membrane filtration water systems; food processing streams and waste treatment systems as well as in clarifiers, liquid-solid applications, municipal sewage treatment systems; and industrial or municipal water distribution systems.

The methods of treating an industrial processing surface with the peroxyformic acid compositions can include a plurality of steps. A first step can be referred to as a product removal step or displacement where product (e.g. contaminants and impurities such as aldehydes and alcohols, etc.) is removed from the industrial processing system. In some aspects, such product can be effectively recovered and used as opposed to discharging as plant effluent. The product removal step can last as long as it takes to remove and recover product from the industrial processing system. In general, it is expected that the product removal step will take at least a couple minutes for most systems.

In a preferred aspect, an on-site and/or in-line generator feeds the peroxyformic acid composition to an industrial processing system. In an aspect, the peroxyformic acid composition is fed into an intake stream, such as a water intake stream, on a periodic basis. In exemplary embodiment, the peroxyformic acid composition is fed into a water intake stream for about 30 minutes about every 4 hours at a desired concentration. In an aspect, from about 25 to about 1,000 ppm peroxyformic acid are dosed to the system, or from about 50 to about 500 ppm peroxyformic acid, or still further from about 50 to about 250 ppm peroxyformic acid.

In an aspect of the invention a controller or programmable device provides scheduled dosing and control of other onsite and/or in-line dosing and delivery of water and/or other actives to the system. In such an aspect a controller is capable of shutting off other chemical feeds at the time of dosing the peroxyformic acid composition. In an exemplary embodiment, a sufficient amount of time is provided for the industrial processing system, such as a scrubber, to be rinsed with only water, including while the peroxyformic acid is being generated. In some embodiments, the amount of time is a few minutes, such as from about 1 to about 15 minutes, or about 1 to about 10 minutes, or about 5 minutes. In an embodiment, the peroxyformic acid can be dosed into the water feed line of the processing system, such as the scrubber, turning the feed water into the peroxyformic acid use solution and treating the processing system, such as the scrubber.

In an exemplary dosing interval the peroxyformic acid composition is dosed on an interval suitable to prevent the growth of microbes and the formation of any biofilm. As referred to herein the interval refers to the amount of time between the dosing of the cleaning composition comprising the peroxyformic acid composition. In an exemplary embodiment, a dosing interval to provide the cleaning composition is at least once a week. In a further embodiment, a dosing interval to provide the cleaning composition is at least once every other day. In a further embodiment, a dosing interval to provide the cleaning composition is at least a day.

In a preferred exemplary embodiment, a dosing interval for the peroxyformic acid composition is particularly suitable to prevent the growth of microbes and the formation of any biofilm, including at an interval of from about 2 to about 10 hours between dosing, or about 3 to about 5 hour interval. Without being limited to a particular mechanism of action according to the present invention, in an exemplary embodiment, a 4 hour dosing interval is suitable based upon the doubling time of most microbes, preventing a biofilm to get a foothold on a surface. In such an embodiment, after about 30 minutes of peroxyformic acid treatment, the controller shuts off the dosing and/or generating of the peroxyformic acid. In an in-line generator embodiment, the shutting off of the dosing allows the inert reagents (e.g. formic acid) to clear the reaction holding line. Thereafter, a chemical supply to the industrial processing system, such as a scrubber, is turned back on (sodium bisulfite, for example) and can be used in the process of the facility.

According to an embodiment of the invention for use of the peroxyformic acid in an ethanol fermentation system, bisulfite and most other additives would need to be shut off during treatment of the surfaces with the peroxyformic acid. Without being limited to a particular mechanism of action, the bisulfite would reduce the peroxyformic acid solution and render it inactive. As a result, in such an embodiment, once the bisulfite stream is turned back on, any residual peroxyformic acid in the system would be eliminated preventing any other downstream effects of active peroxyformic acid, including for example any residual peroxyformic acid as effluent from the system.

The dosing of the peroxyformic acid compositions for contacting the surface in need of treatment is for a sufficient amount of time to contact microorganisms, biofilm and/or other contaminants on the surface. In an aspect, the peroxyformic acid compositions contacts the surface for at least about 15 seconds to about 2 hours, for at least about 30 seconds to about 1 hour, for at least about 45 seconds to about 45 minutes, for at least about 60 seconds to about 30 minutes, or any range of time there between.

In an aspect, the peroxyformic acid compositions contact the surface in a use solution of from about 0.001% to about 0.1% active peroxyformic acid, from about 0.005% to about 0.1% active peroxyformic acid, from about 0.0075% to about 0.01% active peroxyformic acid, or from about 0.0075% to about 0.05% active peroxyformic acid. In a particularly preferred embodiment, the peroxyformic acid compositions contact the surface in a use solution of from about 75 ppm active peroxyformic acid (0.0075%).

The peroxyformic acid and the surface can be contacted to form a treated target composition comprising any suitable concentration of said peroxyformic acid, e.g., at least about 10 ppm, at least about 100 ppm, or preferably from about 10-1,000 ppm of peroxyformic acid. The composition used in the present methods can retain any suitable concentration or percentage of the peroxyformic acid activity for any suitable time after the treated target composition is formed. In some embodiments, the composition used in the present methods retains at least about 50%, 55%, 60%, 65%, 70%, 75%, 80%, 85% or 90% of the initial peroxyformic acid activity for any suitable time after the treated target composition is formed. In other embodiments, the composition used in the present methods retains at least about 60% of the initial peroxyformic acid activity for at least 1, 2, 3, 4, 5, 6, 7, 8, 9, 10, 11, 12, 13, 14, 15, 20, 25, 30 minutes, 1 hour, or 2 hours after the treated target composition is formed.

In an aspect, the methods of the invention for providing the peroxyformic acid composition to a surface in need of treatment can further include an initial step of stopping any flow of $CO_2$ or other processing component. In a further aspect, the treatment can further include an initial step of stopping bisulfite source (or other cleaning agent) from contacting the surface. Still further, the treatment can include a step of treating the surface in combination with the peroxyformic acid (i.e. co-injected), before the peroxyformic acid, and/or after the peroxyformic acid, with one or more of the following agents: a defoaming composition, an additional sanitizing agent, an oxidant, and/or a neutralizing composition for any $CO_2$ on the surface.

In an aspect, the temperature of the surface in need of treatment may be between about 2° C. to 60° C., between about 15° C. to 50° C., between about 18° C. to 40° C., or any range of there between. In an aspect, the temperature of the surface treatment may be ambient temperatures, such as from 20° C. to 30° C.

Beneficially, the methods of treatment do not negatively interfere with the compatibility of the systems or a portion of a processing system, and further do not negatively interfere with the process, such as fermentation, as may be measured by the output of the process. In a beneficial aspect the method of treatment does not result in any negative impact on performance or the effluent from the system. For example, in an exemplary embodiment where the peroxyformic acid is employed in $CO_2$ scrubbers in a fermentation processing system, the peroxyformic acid does not carry through the fermentation and/or distillation process in amounts or concentrations. In a still further preferred embodiment, the peroxyformic acid does not cause animal feeding concerns and/or regulatory concerns by remaining in any product or effluent, such as Dried Distillers Grain (DDG).

The methods of treatment according to the invention provide broad antimicrobial efficacy. In a particular aspects, the methods of treatment according to the invention provide biofilm antimicrobial and biocidal efficacy. Exemplary microorganisms susceptible to the peracid compositions of the invention include, gram positive bacteria (e.g., *Staphylococcus aureus, Bacillus* species (sp.) like *Bacillus subtilis, Clostridia* sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger, Cephalosporium acremonium, Penicillium notatum,* and *Aureobasidium pullulans*), filamentous fungi (e.g., *Aspergillus niger* and *Cladosporium resinae*), algae (e.g., *Chlorella vulgaris, Euglena gracilis,* and *Selenastrum capricornutum*), and other analogous microorganisms and unicellular organisms (e.g., phytoplankton and protozoa). Other exemplary microorganisms susceptible to the peracid compositions of the invention include the exemplary microorganisms disclosed in U.S. patent application US 2010/0160449, e.g., the sulfur- or sulfate-reducing bacteria, such as *Desulfovibrio* and *Desulfotomaculum* species.

The methods of treatment according to the invention provide other contaminant removal, such as mineral scale removal and removal of mineral buildup conventionally found on hard surfaces employed in industrial processing. In a particular aspects, the methods of treatment according to the invention provide scale and mineral removal and prevention of buildup or accumulation. Mineral scales are soluble salts that precipitate out as crystalline mineral scales within a system, such as fermentation, filtration and other industrial processing systems. Examples of mineral scales include calcium carbonate, calcium sulfate, calcium phosphate, barium sulfate, strontium sulfate, iron hydroxide, silicone dioxide (silica), calcium oxalate, etc.

In an aspect, the methods of treatment with the peroxyformic acid compositions can further comprise additional treatment cycles selected from an acidic treatment, an alkaline treatment, an enzymatic treatment and/or a neutral treatment either before or after the peroxyformic acid composition contacts the surface. Another step often used can be referred to as a pre-rinse step. In general, water and/or an alkaline solution can be run through the processing system to remove soils.

In an aspect, an alkaline treatment employs an alkaline use solution to contact the surface at the same time, and/or before, and/or after the peroxyformic acid composition has been applied to the surface. Exemplary alkaline sources suitable for use with the methods of the present invention include, but are not limited to, basic salts, amines, alkanol amines, carbonates and silicates. Other exemplary alkaline sources for use with the methods of the present invention include NaOH (sodium hydroxide), KOH (potassium hydroxide), TEA (triethanol amine), DEA (diethanol amine), MEA (monoethanolamine), sodium carbonate, and morpholine, sodium metasilicate and potassium silicate. The alkaline source selected is compatible with the surface to be cleaned. In some embodiments, the alkaline override use solution includes an activator complex. In other embodiments, an activator complex is applied to the surface prior to the application of an alkaline override use solution. The alkaline override use solution selected is dependent on a variety of factors, including, but not limited to, the type of soil to be removed, and the surface from which the soil is removed. In some embodiments, the pH of the alkaline override use solution is about 10 to about 13. In some embodiments, the pH is about 12. The pH of the alkaline override use solution is formulated to facilitate soil removal from the selected surface, while also being compatible with the selected surface. In some embodiments, the pH of the total solution used to clean the surface, i.e., the pH of the solution after both the active oxygen use solution and the alkaline override use solutions have been applied to the surface, is about 10 to about 11.5.

In an aspect, an acidic treatment employs an acidic use solution to contact the surface at the same time, and/or before, and/or after the peroxyformic acid composition has been applied to the surface. Exemplary acid sources suitable for use with the methods of the present invention include, but are not limited to, mineral acids (e.g., phosphoric acid, nitric acid, sulfuric acid) and organic acids (e.g., lactic acid, acetic acid, hydroxyacetic acid, citric acid, glutamic acid, glutaric acid, methane sulfonic acid, acid phosphonates (e.g., HEDP), and gluconic acid). In some embodiments, the ideal additional acidic component provides good chelation once neutralized by the alkaline override use solution. In some embodiments, the additional acidic component present in the active oxygen use solution includes a carboxylic acid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids for use with the methods of the present invention may include those having one, two, three, or more carboxyl groups.

Cleaning Compositions

In one aspect, the present invention employs peroxyformic acid compositions which may be dosed at a point of use and/or generated in situ at a point of use for the treatment according to the invention. As referred to herein, the peroxyformic acid compositions comprises peroxyformic acid in an suitable type of aqueous composition. For example, the aqueous composition can be an aqueous solution. In another example, the resulting aqueous composition can be an aqueous suspension. The peroxyformic acid compositions can include a range of concentrations of the peracid (w/w) and the hydrogen peroxide (w/w), including at least about 2 to about 1,500, e.g., about 2, 3, 4, 5, 6, 7, 8, 9, 10, or greater.

The peroxyformic acid compositions can include any suitable concentration of hydrogen peroxide, including about 5% (w/w) or less hydrogen peroxide, e.g., about 5% (w/w), 4.5% (w/w), 4% (w/w), 3.5% (w/w), 3% (w/w), 2.5% (w/w), 2% (w/w), 1.5% (w/w), or 1% (w/w) or less hydrogen peroxide.

The peroxyformic acid compositions can include any suitable concentration of peroxyformic acid. In some embodiments, the resulting aqueous composition comprises from about 0.001% (w/w) to about 20% (w/w) peroxyformic acid, e.g., about 0.001%-0.005% (w/w), 0.005%-0.01% (w/w), 0.01%-0.05% (w/w), 0.05%-0.1% (w/w), 0.1%-0.5% (w/w), 0.5%-1% (w/w), 1%-2% (w/w), 2%-3% (w/w), 3%-4% (w/w), 4%-5% (w/w), 5%-6% (w/w), 6%-7% (w/w), 7%-8% (w/w), 8%-9% (w/w), 9%-10% (w/w), 10%-11% (w/w), 11%-12% (w/w) 12%-13% (w/w) 13%-14% (w/w) 14%-15% (w/w) 15%-16% (w/w) 16%-17% (w/w) 17%-18% (w/w) 18%-19% (w/w) 19%-20% (w/w) peroxyformic acid.

The peroxyformic acid compositions according to the invention can comprise a stabilizing agent. Any suitable stabilizing agents can be used. Exemplary stabilizing agents include a phosphonate salt(s) and/or a heterocyclic dicarboxylic acid, e.g., dipicolinic acid. In an aspect, the compositions and/or methods can further comprise using a stabilizing agent for peroxyformic acid, a stabilizing agent for hydrogen peroxide, and/or a pH buffering agent. The present methods can use any suitable stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present methods can use two or more stabilizing agents, e.g., HEDP and 2,6-pyridinedicarboxylic acid (DPA).

In Situ Generated Peroxyformic Acid

Any of the present methods of generating the peroxyformic acid can be conducted at any suitable temperature. In some embodiments, the present methods can be conducted at a temperature ranging from about −2° C. to about 70° C., about 10° C. to about 70° C., e.g., about 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., 55° C.-60° C., 60° C.-65° C., or 65° C.-70° C. In other embodiments, the present methods can be conducted under ambient conditions. In still other embodiments, the present methods can be conducted under heating, e.g., at a temperature ranging from about 30° C.-35° C., 35° C.-40° C., 40° C.-45° C., 45° C.-50° C., 50° C.-55° C., 55° C.-60° C., 60° C.-65° C., or 65° C.-70° C.

The present methods of generating the peroxyformic acid can be conducted in the presence of a catalyst. Any suitable catalyst can be used in the present methods. In some embodiments, the catalyst can be a mineral acid, e.g., sulfuric acid, methanesulfonic acid, nitric acid, phosphoric acid, pyrophosphoric acid, polyphosphoric acid or phosphonic acid.

The present methods of generating the peroxyformic acid can be conducted in the presence of a cation acid exchange resin system. Any suitable cation acid exchange resin system can be used in the present methods. In some embodiments, the cation acid exchange resin system is a strong cation acid exchange resin system. In other embodiments, the acid exchange resin system is sulfonic acid exchange resin, e.g., commercially-available as Dowex M-31 or Nafion.

The resulting aqueous peroxyformic acid composition can comprise a stabilizing agent for the peracid. Any suitable stabilizing agents can be used in the present methods. Exemplary stabilizing agents include a phosphonate salt(s) and/or a heterocyclic dicarboxylic acid, e.g., dipicolinic acid.

The present methods can further comprise a step of reducing the concentration of the hydrogen peroxide in the resulting aqueous composition. The concentration of the hydrogen peroxide in the resulting aqueous composition can be reduced using any suitable methods. For example, the concentration of the hydrogen peroxide in the resulting aqueous composition can be reduced using a catalase or a peroxidase.

The present methods can be used to generate peroxyformic acid in any suitable manner or at any suitable location. In some embodiments, the present methods can be used to generate peroxyformic acid in situ for the application of the formed peroxyformic acid. Exemplary peracid forming compositions including use of an organic acid and an oxidizing agent, such as hydrogen peroxide may be employed to generate a peracid composition in situ. Description of exemplary in situ methods for peracid forming compositions is provided in U.S. Pat. Nos. 8,846,107 and 8,877,254, which are herein incorporated by reference in their entirety.

Controllers and Onsite Generators

In an embodiment of the invention, an in-line peroxyformic acid generator is provided on site to feed peroxyformic acid into a water intake stream on a scheduled basis according to the methods of use. In an aspect, a scheduled dosing of 30 minutes every 4 hours at 75 ppm active peroxyformic acid provides a desired result of preventing biofilm in various industrial processing systems according to the invention. In an aspect, controller capable of timing the dose is responsible for shutting off other chemical feeds at the time of dosing, allowing a sufficient time for the surface (e.g.

scrubber) to rinse with only water, while the peroxyformic acid is being generated (e.g. 5 minutes), then dosing into the water feed line of the surface (e.g. scrubber), turning the feed water into the peroxyformic acid use solution and treating the surface. After the period of peroxyformic acid treatment, e.g. 30 minutes, the controller would shut off the generator, allow the inert acid, e.g. formic acid, to clear the reaction holding line, shut down the reactor, and turn the chemical supply back on (e.g. sodium bisulfite) used in the process of the facility. As one skilled in the art will ascertain, bisulfite and most other additives would need to be shut off during treatment as they would reduce the peroxyformic acid solution and render it inactive. Once the bisulfite stream is turned back on, any residual peroxyformic acid in the system would be eliminated preventing any other downstream effects of active peroxyformic acid.

In certain aspects, the in-line peroxyformic acid generator may include a monitoring and controlling unit that comprises a controller device and a plurality of sensors. Each of the plurality of sensors may be configured to obtain a different characteristic of the chemical feeds and each sensor may also be in communication with the controller. The plurality of sensors can comprise, for example, sensors for measuring conductivity, concentration, pH, oxidation/reduction potential (ORP), fluorescence (or other monitoring visual indicator), biocide concentration, turbidity, temperature, flow, dissolved oxygen (DO), and the like.

Based on signals received from the sensors, the controller may send signals to chemical injection pumps, which are in fluid communication with various chemical feeds, to turn the pumps off (cause them to stop adding chemical) or turn them on (cause them to add a specified amount of more chemical). The components of this automated system may be in communication with each other in any number of ways, including through any combination of wired connection, a wireless connection, electronically, cellularly, through infrared, satellite, or according to any other types of communication networks, topologies, protocols, and standards.

As used herein, the term "controller" or "controller device" refers to a manual operator or an electronic device having components such as a processor, memory device, digital storage medium, a communication interface including communication circuitry operable to support communications across any number of communication protocols and/or networks, a user interface (e.g., a graphical user interface that may include cathode ray tube, liquid crystal display, plasma display, touch screen, or other monitor), and/or other components. The controller is preferably operable for integration with one or more application-specific integrated circuits, programs, computer-executable instructions or algorithms, one or more hard-wired devices, wireless devices, and/or one or more mechanical devices. Moreover, the controller is operable to integrate the feedback, feed-forward, or predictive loop(s) of the invention. Some or all of the controller system functions may be at a central location, such as a network server, for communication over a local area network, wide area network, wireless network, internet connection, microwave link, infrared link, wired network (e.g., Ethernet) and the like. In addition, other components such as a signal conditioner or system monitor may be included to facilitate signal transmission and signal-processing algorithms.

The disclosed monitoring and controlling system provides methods to generate real-time, on-line, reliable data from the water of the industrial system. Based upon the data received by the controller from the plurality of sensors, real-time adjustments can be made to the water. For example, the plurality of sensors may provide continuous or intermittent feedback, feed-forward, or predictive information to the controller, which can relay this information to a relay device, such as the Nalco Global Gateway, which can transmit the information via cellular communications to a remote device, such as a cellular telephone, computer, or any other device that can receive cellular communications. This remote device can interpret the information and automatically send a signal (e.g. electronic instructions) back, through the relay device, to the controller to cause the controller to make certain adjustments to the output of the chemical injection pumps. The information may also be processed internally by the controller and the controller can automatically send signals to the pumps, to adjust the amount of chemical injection. Based upon the information received by the controller from the plurality of sensors or from the remote device, the controller can transmit signals to the various pumps to make automatic, real-time adjustments, to the amount of chemical that the pumps are injecting into the water of the system.

In certain aspects, the remote device or controller can include appropriate software to receive data from the plurality of sensors and determine if the data indicates that one or more measured properties of the water are within, or outside, an acceptable range. The software can also allow the controller or remote device to determine appropriate actions that should be taken to remedy the property that is outside of the acceptable range. The monitoring and controlling system and/or controller disclosed herein can incorporate programming logic to convert analyzer signals from the plurality of sensors to pump adjustment logic and, in certain embodiments, control one or more of a plurality of chemical injection pumps with a unique basis.

Data transmission of measured properties or signals to chemical pumps, alarms, remote monitoring devices, such as computers or cellular telephones, or other system components is accomplished using any suitable device, and across any number of wired and/or wireless networks, including as examples, WiFi, WiMAX, Ethernet, cable, digital subscriber line, Bluetooth, cellular technologies, etc. The Nalco Global Gateway is an example of a suitable device. Any suitable interface standard(s), such as an Ethernet interface, wireless interface (e.g., IEEE 802.11a/b/g/x, 802.16, Bluetooth, optical, infrared, radiofrequency, etc.), universal serial bus, telephone network, the like, and combinations of such interfaces/connections may be used. As used herein, the term "network" encompasses all of these data transmission methods. Any of the described devices (e.g., archiving systems, data analysis stations, data capturing devices, process devices, remote monitoring devices, chemical injection pumps, etc.) may be connected to one another using the above-described or other suitable interface or connection.

Formic Acid and Hydrogen Peroxide

In an aspect, peroxyformic acid compositions generated in situ comprise contacting formic acid with hydrogen peroxide to form a resulting aqueous composition that comprises a peracid that comprises peroxyformic acid. Additional disclosure of suitable in situ reaction for the generation of peroxyformic acid is disclosed in application Ser. No. 14/972,308, titled Methods for Forming Peroxyformic Acid and Uses Thereof, which is herein incorporated by reference in its entirety.

In an aspect, before said contacting, the ratio between the concentration of said formic acid (w/v) and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher within preferably about 1 hour, or preferably within about 10 minutes of said contacting.

The formic acid used in the present methods can be provided in any suitable way. In some embodiments, before the contacting step, the formic acid can be provided in a composition that comprises formic acid, e.g., an aqueous solution that comprises formic acid. In other embodiments, before the contacting step, the formic acid can be provided in a composition that comprises a substance that generates formic acid upon contact with an aqueous composition. Any suitable substance that generates formic acid can be used in the present methods. The substance can be a salt of formate, e.g., a sodium or ammonium salt of formate, or an ester of formate. Exemplary esters of formate include glycerol formates, pentaerythritol formates, mannitol formates, propylene glycol formates, sorbitol formates and sugar formates. Exemplary sugar formates include sucrose formates, dextrin formates, maltodextrin formates, and starch formates. In some embodiments the formates may be provided in a solid composition, such as a starch formate.

The hydrogen peroxide used in the present methods can be provided in any suitable way. In some embodiments, before the contacting step, the hydrogen peroxide can be provided in a composition that comprises hydrogen peroxide, e.g., an aqueous solution that comprises hydrogen peroxide. In other embodiments, before the contacting step, the hydrogen peroxide can be provided in a composition that comprises a substance that generates hydrogen peroxide upon contact with an aqueous composition. Any suitable substance that generates hydrogen peroxide can be sued in the present methods. The substance can comprise a precursor of hydrogen peroxide. Any suitable precursor of hydrogen peroxide can be used in the present methods. For example, the precursor of hydrogen peroxide can be sodium percarbonate, sodium perborate, urea hydrogen peroxide, or PVP-hydrogen peroxide.

In some embodiments, formic acid provided in a first aqueous composition is contacted with hydrogen peroxide provided in a second aqueous composition to form peroxyformic acid in the resulting aqueous composition. In other embodiments, formic acid provided in a first aqueous composition is contacted with a substance that generates hydrogen peroxide upon contact with an aqueous composition provided in a second solid composition to form peroxyformic acid in the resulting aqueous composition. In still other embodiments, a substance that generates formic acid upon contact with an aqueous composition provided in a first solid composition is contacted with hydrogen peroxide provided in a second aqueous composition to form peroxyformic acid in the resulting aqueous composition. In yet other embodiments, a substance that generates formic acid upon contact with an aqueous composition provided in a first solid composition and a substance that generates hydrogen peroxide upon contact with an aqueous composition provided in a second solid composition are contacted with a third aqueous composition to form peroxyformic acid in the resulting aqueous composition. In yet other embodiments, a substance that generates formic acid upon contact with an aqueous composition and a substance that generates hydrogen peroxide upon contact with an aqueous composition are provided in a first solid composition, and the first solid composition is contacted with a second aqueous composition to form peroxyformic acid in the resulting aqueous composition.

The resulting aqueous composition that comprises peroxyformic acid can be any suitable types of aqueous compositions. For example, the resulting aqueous composition can be an aqueous solution. In another example, the resulting aqueous composition can be an aqueous suspension.

Before the contacting step, the ratio between the concentration of the formic acid (w/v) and the concentration of the hydrogen peroxide (w/v) can be in any suitable range. In some embodiments, before the contacting, the ratio between the concentration of the formic acid (w/v) and the concentration of the hydrogen peroxide (w/v) can be from about 2 to about 100, e.g., about 2-3, 3-4, 4-5, 5-6, 6-7, 7-8, 8-9, 9-10, 10-15, 15-20, 20-25, 25-30, 30-35, 35-40, 40-45 or 45-50 or greater from about 50-100.

The ratio between the concentration of the peracid (w/w) and the concentration of hydrogen peroxide (w/w) in the formed aqueous composition can reach any suitable range. In some embodiments, the ratio between the concentration of the peracid (w/w) and the concentration of hydrogen peroxide (w/w) in the formed aqueous composition can reach, within about 4 hours, or preferably 2 hours of the contacting, from about 2 to about 1,500, e.g., about 2-3, 3-4, 4-5, 5-6, 6-7, 7-8, 8-9, 9-10, 10-15, 15-20, 20-25, 25-30, 30-35, 35-40, 40-45, 45-50, 50-60, 60-70, 70-80, 80-90, 90-100, 100-200, 200-300, 300-400, 400-500, 500-600, 600-700, 700-800, 800-900, 900-1,000, 1,000-1,100, 1,100-1,200, 1,200-1,300, 1,300-1,400, or 1,400-1,500. In other embodiments, the ratio between the concentration of the peracid (w/w) and the concentration of hydrogen peroxide (w/w) in the formed aqueous composition reaches at least about 10 within about 30 minutes of the contacting, preferably at least about 10-40 within about 30 minutes of the contacting.

The formed aqueous composition can comprise any suitable concentration of hydrogen peroxide. In some embodiments, the formed aqueous composition can comprise about 5% (w/w) or less hydrogen peroxide, e.g., about 5% (w/w), 4.5% (w/w), 4% (w/w), 3.5% (w/w), 3% (w/w), 2.5% (w/w), 2% (w/w), 1.5% (w/w), 1% (w/w), 0.9% (w/w), 0.8% (w/w), 0.7% (w/w), 0.6% (w/w), 0.5% (w/w), 0.4% (w/w), 0.3% (w/w), 0.2% (w/w), 0.1% (w/w), 0.05% (w/w), 0.01% (w/w), 0.005% (w/w), or 0.001% (w/w) of hydrogen peroxide. In other embodiments, the formed aqueous composition reaches about 2% (w/w) or less hydrogen peroxide within about 1 hour, or preferably within about 10 minutes of the contacting. In still other embodiments, the formed aqueous composition reaches about 1% (w/w) or less hydrogen peroxide within about 1 hour of the contacting. In yet other embodiments, the formed aqueous composition reaches about 0% (w/w) to about 0.001% (w/w) hydrogen peroxide and maintains about 0% (w/w) to about 0.001% (w/w) hydrogen peroxide for about 1 hour.

The resulting aqueous composition can comprise any suitable concentration of peroxyformic acid. In some embodiments, the resulting aqueous composition comprises from about 0.001% (w/w) to about 20% (w/w) peroxyformic acid, e.g., about 0.001%-0.005% (w/w), 0.005%-0.01% (w/w), 0.01%-0.05% (w/w), 0.05%-0.1% (w/w), 0.1%-0.5% (w/w), 0.5%-1% (w/w), 1%-2% (w/w), 2%-3% (w/w), 3%-4% (w/w), 4%-5% (w/w), 5%-6% (w/w), 6%-7% (w/w), 7%-8% (w/w), 8%-9% (w/w), 9%-10% (w/w), 10%-11% (w/w), 11%-12% (w/w) 12%-13% (w/w) 13%-14% (w/w) 14%-15% (w/w) 15%-16% (w/w) 16%-17% (w/w) 17%-18% (w/w) 18%-19% (w/w) 19%-20% (w/w) peroxyformic acid.

The formic acid and the hydrogen peroxide can be contacted in the absence of a $C_2$-$C_{22}$ carboxylic acid and/or a $C_2$-$C_{22}$ percarboxylic acid and the peracid in the formed aqueous composition comprises peroxyformic acid only.

The formic acid and hydrogen peroxide can be contacted in the presence of a $C_2$-$C_{22}$ carboxylic acid and the peracid in the formed aqueous composition comprises peroxyformic acid and the $C_2$-$C_{22}$ percarboxylic acid. Any suitable $C_2$-$C_{22}$ carboxylic acid can be used in the present methods. In some embodiments, the $C_2$-$C_{22}$ carboxylic acid is acetic acid, octanoic acid and/or sulfonated oleic acid, and the peracid in the formed aqueous composition comprises peroxyformic acid and one or more of peroxyacetic acid, peroxyoctanoic acid and peroxysulfonated oleic acid.

The formic acid provided in a first aqueous composition can be contacted with the hydrogen peroxide provided in a second aqueous composition that also comprises peroxyacetic acid to form a resulting aqueous composition that comprises a total peracid that comprises peroxyformic acid and peroxyacetic acid. Before the contacting step, the ratio between the concentration of the formic acid (w/v) and the concentration of the hydrogen peroxide (w/v) can be at any suitable range. The ratio between the concentration of total peracid (w/w) and the concentration of hydrogen peroxide (w/w) in the resulting aqueous composition can also reach any suitable range. In some embodiments, before the contacting, the ratio between the concentration of the formic acid (w/v) and the concentration of the hydrogen peroxide (w/v) can be about 5 or higher and the ratio between the concentration of total peracid (w/w) and the concentration of hydrogen peroxide (w/w) in the resulting aqueous composition reaches at least about 5 within about 2 minutes of the contacting. In other embodiments, the ratio between the concentration of total peracid (w/w) and the concentration of hydrogen peroxide (w/w) in the resulting aqueous composition can reach at least about 10 within about 20 minutes of the contacting. In yet other embodiments, before the contacting, the ratio between the concentration of the formic acid (w/v) and the concentration of the hydrogen peroxide (w/v) can be about 20 or higher and the ratio between the concentration of total peracid (w/w) and the concentration of hydrogen peroxide (w/w) in the resulting aqueous composition can reach at least about 10 within at least about 1 minute of the contacting. The concentration of hydrogen peroxide (w/w) in the resulting aqueous composition can reach any suitable concentration. In some embodiments, the concentration of hydrogen peroxide (w/w) in the resulting aqueous composition can reach about 0% (w/w) to about 0.001% (w/w) hydrogen peroxide within at least about 4 hours, or preferably 2 hours of the contacting. In other embodiments, the concentration of hydrogen peroxide (w/w) in the resulting aqueous composition can remain at about 0% (w/w) to about 0.001% (w/w) for least 1 hour.

Esters and Hydrogen Peroxide

In an aspect, peroxyformic acid compositions generated in situ comprise contacting an ester of a polyhydric alcohol and formic acid and hydrogen peroxide or a substance that generates hydrogen peroxide when in contact with a liquid to form a resulting aqueous composition that comprises a peracid that comprises peroxyformic acid. Additional disclosure of suitable in situ reaction for the generation of peroxyformic acid is disclosed in application Ser. No. 14/973,389, titled Generation of Peroxyformic Acid Through Polyhydric Alcohol Formate, which is herein incorporated by reference in its entirety.

In one aspect, the present invention is directed to a peroxyformic acid forming composition comprising: a) a first reagent that comprises an ester of a polyhydric alcohol and formic acid, and b) a second reagent that comprises hydrogen peroxide or that comprises a substance that generates hydrogen peroxide when in contact with a liquid, wherein 1) said first reagent and said second reagent are kept separately prior to use, and when it is time to generate peroxyformic acid, said first reagent and said second reagent are configured to be contacted with each other to form a liquid that comprises peroxyformic acid and has a pH below about 11, and pH of the formed liquid becomes about 8 or lower within about 1 minute after the contact between said first reagent and said second reagent; or 2) said second reagent comprises a substance that generates hydrogen peroxide when in contact with a liquid, said first reagent and said second reagent are comprised in a solid composition, and when it is time to generate peroxyformic acid, said solid composition is configured to be contacted with a liquid to form a liquid that comprises peroxyformic acid and has a pH below about 11, and pH of the formed liquid becomes about 8 or lower within about 1 minute after the contact between said solid composition and said liquid.

In some embodiments, the present peroxyformic acid forming composition comprises a) a first reagent that comprises an ester of a polyhydric alcohol and formic acid, and b) a second reagent that comprises hydrogen peroxide or that comprises a substance that generates hydrogen peroxide when in contact with a liquid, wherein said first reagent and said second reagent are kept separately prior to use, and when it is time to generate peroxyformic acid, said first reagent and said second reagent are configured to be contacted with each other to form a liquid that comprises peroxyformic acid and has a pH below about 11, and pH of the formed liquid becomes about 8 or lower within about 1 minute after the contact between said first reagent and said second reagent. In other embodiments, the present peroxyformic acid forming composition comprises a) a first reagent that comprises an ester of a polyhydric alcohol and formic acid, and b) a second reagent that comprises a substance that generates hydrogen peroxide when in contact with a liquid, wherein said first reagent and said second reagent are comprised in a solid composition, and when it is time to generate peroxyformic acid, said solid composition is configured to be contacted with a liquid to form a liquid that comprises peroxyformic acid and has a pH below about 11, and pH of the formed liquid becomes about 8 or lower within about 1 minute after the contact between said solid composition and said liquid.

The present peroxyformic acid forming compositions can comprise any suitable ester of a polyhydric alcohol and formic acid. Typically, a polyhydric alcohol refers to a molecule with two or more hydroxyl (—OH) groups. An ester of a polyhydric alcohol and formic acid refers to an ester formed between a polyhydric alcohol and formic acid. Esters as referred to herein are considered 'water-less' systems as no additional water is added to the reaction. In some embodiments, the present peroxyformic acid forming compositions comprise glycerol formates, pentaerythritol formates, mannitol formates, propylene glycol formates, sorbitol formates and sugar formates. The present peroxyformic acid forming compositions can comprise any suitable sugar formates, e.g., sucrose formates, dextrin formates, maltodextrin formates, or starch formates.

In a preferred embodiment, a liquid reaction employs glycerol formates, pentaerythritol formates, mannitol formates, or propylene glycol formates. In a still further preferred embodiment, a liquid reaction employs glycerol formates. Beneficially, the glycerol formates rapidly undergo hydrolysis for peroxyformic acid generation according to the methods of the invention. In an aspect, the precursors provided do not include additional water added into the system which would negatively interfere with the kinetics of the reaction between the ester of a polyhydric alcohol and formic acid and hydrogen peroxide. In an aspect, the premixes and the peroxyformic acid forming composition do not add free water into the systems, which would negatively interfere with the ester, e.g. glycerol formates.

In a preferred embodiment, a solid reaction employs sugar formates e.g., sucrose formates, dextrin formates, maltodextrin formates, or starch formates. In a still further preferred embodiment, a solid reaction employs starch formates.

The present peroxyformic acid forming compositions can comprise a use solution or a concentrate of the ester of a polyhydric alcohol and formic acid. In some aspects, the methods of the invention generate a peroxyformic acid through a concentrate reaction of the ester of a polyhydric alcohol and formic acid. In other aspects, the methods of the invention generate a peroxyformic acid through a diluted use solution reaction of the ester of a polyhydric alcohol and formic acid.

The first or second reagent can have any suitable pH range in the present peroxyformic acid forming compositions. For example, the first or second reagent can have a pH below about 11, or from about −2 to about 11, or from about 0 to about 11, e.g., about −2 to about −1, −2 to about 0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the first or second reagent has a pH ranging from about 5 to about 10, e.g., about 5-6, 5-7, 5-8, 5-9, 5-10, 6-7, 6-8, 6-9, 6-10, 7-8, 7-9, 7-10, 8-9, 8-10, or 9-10. In other embodiments, the first or second reagent has a pH at about 9.

The first reagent and the second reagent can be configured to be contacted with each other to form a liquid, e.g., a solution, that comprises peroxyformic acid and has any suitable pH, including a pH below about 11, or from about −2 to about 11, or from about 0 to about 11, e.g., about −2 to about −1, −2 to about 0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the first reagent and the second reagent are configured to be contacted with each other to form a liquid, e.g., a solution, that comprises peroxyformic acid and has a pH ranging from about −2 to about 11, 0 to about 10, or 5 to about 10, e.g., about −2-0, 0-1, 1-2, 2-3, 3-4, 4-5, 5-6, 5-7, 5-8, 5-9, 5-10, 6-7, 6-8, 6-9, 6-10, 7-8, 7-9, 7-10, 8-9, 8-10, 9-10, or 10-11. In other embodiments, the first reagent and the second reagent are configured to be contacted with each other to form a liquid, e.g., a solution, that comprises peroxyformic acid and has a pH at about 9. In a preferred aspect, the formed liquid, e.g., a solution, that comprises peroxyformic acid and has a pH near neutral, from about 6-7.

The pH of the formed liquid can become about 8 or lower within about 1 minute after the contact between the first reagent and the second reagent or after the contact between the solid composition and the liquid. In some embodiments, the pH of the formed liquid can become about 8 or lower within about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds after the contact between the first reagent and the second reagent or after the contact between the solid composition and the liquid. In other embodiments, the pH of the formed liquid comprising peroxyformic acid becomes about 8 or lower within about 1 minute or less. In an aspect, the pH of the formed liquid comprising peroxyformic acid becomes about 8 or lower within about 45 seconds or less, 40 seconds or less, 35 seconds or less, 30 seconds or less, 25 seconds or less, 20 seconds or less, 15 seconds or less, 10 seconds or less, or 5 seconds or less. In an aspect, the pH of the formed liquid comprising peroxyformic acid becomes about 8 or lower near instantaneously. In other embodiments, the pH of the formed liquid can become about lower than −2, −1, 0, 1, 2, 3, 4, 5, 6, 7, or 8 within about 1 minute after the contact between the first reagent and the second reagent or after the contact between the solid composition and the liquid.

The liquid that comprises peroxyformic acid can maintain the pH ranging from about −2 to about 8, or from about 0 to about 8 for any suitable time after the contact between the first reagent and the second reagent, or after the contact between the composition and a liquid. In some embodiments, the liquid that comprises peroxyformic acid maintains the pH ranging from about −2 to about 8, or from about 0 to about 8 from about 1 second to about 10 hours after the contact between the first reagent and the second reagent or after the contact between the composition and a liquid. For example, the liquid that comprises peroxyformic acid can maintain the pH at about −2, −1, 0, 1, 2, 3, 4, 5, 6, 7, or 8 from about 1 second to about 10 hours after the contact between the first reagent and the second reagent or after the contact between the composition and a liquid. In another example, the liquid that comprises peroxyformic acid can maintain the pH ranging from about 0 to about 8 for about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In a preferred aspect, the formed liquid, e.g., a solution, that comprises peroxyformic acid and has a pH near neutral, from about 6-7 in a use solution.

In some embodiments, the first reagent and the second reagent are configured to be contacted with each other to form a solution that comprises peroxyformic acid and has a pH ranging from about 4 to about 8 or 9, e.g., about 4-5, 5-6, 6-7, 7-8, or 8-9. In a preferred aspect, the formed liquid, e.g., a solution, that comprises peroxyformic acid and has a pH near neutral, from about 6-7 in a use solution. In one example, the first reagent and the second reagent are configured to be contacted with each other to form a solution that comprises peroxyformic acid and has a pH ranging from about 6 to about 8 or 9. The first reagent and the second reagent can be configured to be contacted with each other to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours.

In other embodiments, the solid composition is configured to be contacted with a liquid to form a solution that comprises peroxyformic acid and has a pH ranging from about 4 to about 8 or 9, e.g., about 4-5, 5-6, 6-7, 7-8, or 8-9. In one example, the solid composition is configured to be contacted with a liquid to form a solution that comprises peroxyformic acid and has a pH ranging from about 6 to about 8 or 9. The solid composition is configured to be contacted with a liquid to form a solution that comprises peroxyformic acid and has a pH ranging from about 4 to about 8 or 9, and the solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In a preferred aspect, the formed liquid, e.g., a solution, that comprises peroxyformic acid and has a pH near neutral, from about 6-7 in a use solution.

The first reagent and the second reagent can be configured to be contacted with each other to form a liquid, e.g., a solution, that comprises peroxyformic acid under any suitable conditions or temperature. In some embodiments, the first reagent and the second reagent are configured to be contacted with each other to form a liquid, e.g., a solution, that comprises peroxyformic acid under ambient conditions. In other embodiments, the first reagent and the second reagent are configured to be contacted with each other to form a liquid, e.g., a solution, that comprises peroxyformic acid at a temperature ranging from about −2° C. to about 60° C., 0° C. to about 60° C., or 4° C. to about 60° C., e.g., about −2° C.-0° C., 0° C.-4° C., 4° C.-5° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C. In still other embodiments, the first reagent and the second reagent are configured to be contacted with each other to form a liquid, e.g., a solution, that comprises peroxyformic acid at a temperature at about 4° C. or lower than 4° C., e.g., at about 3° C., 2° C., 1° C., 0° C., or lower than 0° C.

The solid composition can be configured to be contacted with a liquid to form a liquid, e.g., a solution, that comprises peroxyformic acid under any suitable conditions or temperature. In some embodiments, the solid composition can be configured to be contacted with a liquid to form a liquid, e.g., a solution, that comprises peroxyformic acid under ambient conditions. In other embodiments, the solid composition can be configured to be contacted with a liquid to form a liquid, e.g., a solution, that comprises peroxyformic acid at a temperature ranging from about −2° C. to about 60° C., 0° C. to about 60° C., or 4° C. to about 60° C., e.g., about −2° C.-0° C., 0° C.-4° C., 4° C.-5° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., or 55° C.-60° C. In still other embodiments, the solid composition can be configured to be contacted with a liquid to form a liquid, e.g., a solution, that comprises peroxyformic acid at a temperature at about 4° C. or lower than 4° C., e.g., at about 3° C., 2° C., 1° C., 0° C., or lower than 0° C.

The present peroxyformic acid forming compositions can comprise any suitable concentration of an ester of a polyhydric alcohol and formic acid. For example, the first reagent of the peroxyformic acid forming composition can comprise any suitable concentration of an ester of a polyhydric alcohol and formic acid. In some embodiments, the formed liquid is a concentrate and comprises the first reagent in an amount up to about 90% of an ester of a polyhydric alcohol and formic acid. In other embodiments, the formed liquid comprises the first reagent in an amount from about 1 ppm to about 500,000 ppm of an ester of a polyhydric alcohol and formic acid, or from about 10 ppm to about 500,000 ppm of an ester of a polyhydric alcohol and formic acid. For example, the first reagent in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the first reagent in the formed liquid can comprise from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

In another example, the solid composition of the peroxyformic acid forming composition can comprise any suitable concentration of an ester of a polyhydric alcohol and formic acid. In some embodiments, the solid composition can provide a concentrate formed liquid that comprises the first reagent in an amount up to about 90% of an ester of a polyhydric alcohol and formic acid. In other embodiments, the solid composition can provide for the formed liquid from about 10 ppm to about 500,000 ppm of an ester of a polyhydric alcohol and formic acid. For example, the solid composition can provide for the formed liquid the ester of a polyhydric alcohol and formic acid in amounts comprising from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, 90,000-100,000 ppm, 100,000-150,000 ppm, 150,000-200,000 ppm, 200,000-250,000 ppm, 250,000-300,000 ppm, 300,000-350,000 ppm, 350,000-400,000 ppm, 400,000-450,000 ppm, or 450,000-500,000 ppm. In other embodiments, the solid composition can provide for the formed liquid from about 50 ppm to about 40,000 ppm of an ester of a polyhydric alcohol and formic acid, e.g., 50-100, 50-500, 50-1,000, 50-1,500, 50-2,000, 50-2,500, 50-3,000, 50-3,500, 50-4,000, 50-4,500, 50-5,000, 50-10,000, 50-20,000, 50-30,000, or 50-40,000 ppm of an ester of a polyhydric alcohol and formic acid.

The present peroxyformic acid forming compositions can comprise any suitable concentration of hydrogen peroxide or a substance that generates hydrogen peroxide upon contact with a liquid. For example, the second reagent of the peroxyformic acid forming composition can comprise any suitable concentration of hydrogen peroxide. In some embodiments, a concentrate formed liquid comprises the second reagent in an amount up to about 10% of hydrogen peroxide. In some embodiments, the formed liquid comprises the second reagent in an amount comprising about 0.1 ppm to about 100,000 ppm of hydrogen peroxide, or about 0.1 ppm to about 100,000 ppm of hydrogen peroxide. For example, the second reagent in the formed liquid can comprise from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm, 100,000-150,000 ppm, 150,000-200,000 ppm, 200,000-250,000 ppm, or 250,000-300,000 ppm hydrogen peroxide. In other embodiments, the second reagent in the formed liquid comprises from about 150 ppm to about 50,000 ppm of hydrogen peroxide, e.g., about 150-200, 150-300, 150-400, 150-500, 150-600, 150-700, 150-800, 150-900, 150-1,000, 150-1,500, 150-2,000, 150-2,500, 150-3,000, 150-3,500, 150-4,000, 150-4,500, 150-5,000, 150-10,000, 50-20,000, 50-30,000, 50-40,000 or 50-50,000 ppm of hydrogen peroxide.

In some embodiments, a concentrate formed liquid comprises the second reagent in an amount up to about 10% of hydrogen peroxide. In another example, the solid composition can comprise a substance at an amount or concentration that generates from about 0.1 ppm to about 100,000 ppm of hydrogen peroxide upon contact with a liquid in the formed liquid. For example, the solid composition can comprise a substance at an amount or concentration that generates from about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, 4,500-5,000 ppm, 5,000-5,500 ppm, 5,500-6,000 ppm, 6,000-6,500 ppm, 6,500-7,000 ppm, 7,000-7,500 ppm, 7,500-8,000 ppm, 8,000-8,500 ppm, 8,500-9,000 ppm, 9,000-10,000 ppm, 10,000-20,000 ppm, 20,000-30,000 ppm, 30,000-40,000 ppm, 40,000-50,000 ppm, 50,000-60,000 ppm, 60,000-70,000 ppm, 70,000-80,000 ppm, 80,000-90,000 ppm, or 90,000-100,000 ppm hydrogen peroxide.

The present peroxyformic acid forming compositions can be configured to form a liquid, e.g., a solution, that comprises any suitable concentration of peroxyformic acid. For example, the first reagent and the second reagent in the present peroxyformic acid forming compositions can be configured to be contacted with each other to form a liquid and/or solid, e.g., a solution, that comprises any suitable concentration of peroxyformic acid. In some embodiments, the first reagent and the second reagent can be configured to be contacted with each other to form a liquid, e.g., a solution, that comprises from about 0.1 ppm to about 100,000 ppm of peroxyformic acid, from about 0.1 ppm to about 10,000 ppm of peroxyformic acid, or from about 0.1 ppm to about 5,000 ppm of peroxyformic acid, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm or greater of peroxyformic acid. In other embodiments, the first reagent and the second reagent can be configured to be contacted with each other to form a liquid, e.g., a solution, that comprises from about 1 ppm to about 500 ppm of peroxyformic acid, e.g., about 0.1-1 ppm, 0.1-10 ppm, 0.1-20 ppm, 0.1-30 ppm, 0.1-40 ppm, 0.1-50 ppm, 0.1-60 ppm, 0.1-70 ppm, 0.1-80 ppm, 0.1-90 ppm, 0.1-100 ppm, 0.1-150 ppm, 0.1-200 ppm, 0.1-250 ppm, 0.1-300 ppm, 0.1-350 ppm, 0.1-400 ppm, 0.1-450 ppm, 0.1-500 ppm of peroxyformic acid. In still other embodiments, the first reagent and the second reagent can be configured to be contacted with each other to form a liquid, e.g., a solution, that comprises from about 50 ppm to about 100 ppm of peroxyformic acid, e.g., about 50-60 ppm, 60-70 ppm, 70-80 ppm, 80-90 ppm or 90-100 ppm of peroxyformic acid. In yet other embodiments, the first reagent and the second reagent can be configured to be contacted with each other to form a liquid, e.g., a solution, that comprises from about 200 ppm to about 300 ppm of peroxyformic acid, e.g., about 200-210 ppm, 210-220 ppm, 220-230 ppm, 230-240 ppm, 240-250 ppm, 250-260 ppm, 260-270 ppm, 270-280 ppm, 280-290 ppm, 290-300 ppm of peroxyformic acid.

In an aspect, at least about 1 ppm peroxyformic is generated within less than 1 minute of contacting the first reagent and the second reagent. In an aspect, at least about 1 ppm peroxyformic is generated within less than about 55 seconds, 50 seconds or less, 45 seconds or less, 40 seconds or less, 35 seconds or less, 30 seconds or less, 25 seconds or less, 20 seconds or less, 15 seconds or less, 10 seconds or less, or 5 seconds or less. In an aspect, the reaction to form a liquid comprising at least about 1 ppm peroxyformic acid is near instantaneous.

Additional Peracids

The peroxyformic acid formed using the present methods (present composition) can further comprise other percarboxylic acids. A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein. Various embodiments of the invention referring to peroxyformic acid compositions and/or peroxyformic acid solutions are further understood to optionally comprise additional percarboxylic acids. As used herein, the term "peracid" may also be referred to as a "percarboxylic acid" or "peroxyacid." Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyformic acid, peroxyacetic acid and/or peroxyoctanoic acid. Other combinations of mixed peracids are well suited for use in the current invention. Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Water

The peroxyformic acid compositions according to the invention may comprise water in amounts that vary depending upon techniques for processing the composition. Water provides a medium which dissolves, suspends, or carries the other components of the composition. Water can also function to deliver and wet the composition of the invention on an object.

In some embodiments, water makes up a large portion of the composition of the invention and may be the balance of the composition apart from peroxyformic acid composition. The water amount and type will depend upon the nature of the composition as a whole, the environmental storage, and method of application including concentration composition, form of the composition, and intended method of delivery, among other factors. Notably the carrier should be chosen and used at a concentration which does not inhibit the efficacy of the functional components in the composition of the invention for the intended use.

Additional Functional Ingredients

The components of the peroxyformic acid compositions can further be combined with various functional components suitable for use in membrane treatment. In some embodiments, the peroxyformic acid compositions make up a large amount, or even substantially all of the treatment composition for the membranes as disclosed herein. For example, in some embodiments few or no additional functional ingredients are disposed therein.

In other embodiments, additional functional ingredients may be included in the compositions. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used.

In some embodiments, the peroxyformic acid compositions may include surfactants, such as for example nonionic and anionic surfactants, defoaming agents, anti-redeposition agents, bleaching agents, solubility modifiers, dispersants, rinse aids, metal protecting agents, stabilizing agents, corrosion inhibitors, sequestrants and/or chelating agents, wetting agents, water conditioning agents or chelants, enzymes, fragrances and/or dyes, rheology modifiers or thickeners, hydrotropes or couplers, buffers, solvents and the like.

Builders

The present compositions can include a builder. Builders include chelating agents (chelators), sequestering agents (sequestrants), and the like. The builder may act to stabilize the cleaning composition or use solution. Examples of builders include, but are not limited to, phosphonates, phosphates, aminocarboxylates and their derivatives, pyrophosphates, polyphosphates, ethylenediamene and ethylenetriamene derivatives, hydroxyacids, and mono-, di-, and tri-carboxylates and their corresponding acids. Other exemplary builders include aluminosilicates, nitroloacetates and their derivatives, and mixtures thereof. Still other exemplary builders include aminocarboxylates, including salts of ethylenediaminetetraacetic acid (EDTA), hydroxyethylene-diaminetetraacetic acid (HEDTA), and diethylenetriaminepentaacetic acid. For a further discussion of chelating agents/sequestrants, see Kirk-Othmer, Encyclopedia of Chemical Technology, Third Edition, volume 5, pages 339-366 and volume 23, pages 319-320, which is incorporated in its entirety. According to an aspect of the invention, preferred builders are water soluble, biodegradable and phosphorus-free. The amount of builder in the cleaning composition or use solution, if present, is typically between about 10 ppm and about 1000 ppm in the cleaning composition or use solution.

Acidulants, Catalysts and Enzymes

Acidulants may be included as additional functional ingredients in a composition according to the invention. In an aspect, a strong mineral acid such as nitric acid, sulfuric acid, phosphoric acid or a stronger organic acid such as methyl sulfonic acid (MSA) can be used. The combined use of a strong mineral acid or stronger organic acid with the peracid composition provides enhanced antimicrobial efficacy. In addition, some strong mineral and organic acids, such as nitric acid, provide a further benefit of reducing the risk of corrosion toward metals contacted by the peracid compositions according to the invention. In some embodiments, the present composition does not comprise a mineral acid or a strong mineral acid.

In an aspect, the methods of forming the peroxyformic acid may be conducted in the presence of a catalyst. Any suitable catalyst can be used in the present methods. In some embodiments, the catalyst can be a mineral or strong organic acid, e.g., sulfuric acid, methanesulfonic acid, nitric acid, phosphoric acid, pyrophosphoric acid, polyphosphoric acid or phosphonic acid. Such catalysts may be present in peroxyformic acid forming composition in an amount of at least about 0 wt-% to about 10 wt-%, preferably at least about 0.1 wt-% to about 5 wt-%, more preferably from about 1 wt-% to about 5 wt-%.

In some aspects, the present methods can further comprise using a catalyst or an enzyme that catalyzes formation of peroxyformic acid, such as from the ester of a polyhydric alcohol and formic acid, and hydrogen peroxide. The present methods can use any suitable catalyst or enzyme, e.g., a perhydrolytic enzyme, lipase, coronase, termanyl or esperease. The catalyst or an enzyme can be comprised in any suitable reagent. In some embodiments, the first reagent comprises the catalyst or enzyme. In other embodiments, the second reagent comprises the catalyst or enzyme. In still other embodiments, the present methods can further comprise using a third reagent that comprises the catalyst or enzyme. In yet other embodiments, the solid composition comprises the catalyst or enzyme.

Acidulants, catalysts and/or enzymes may be employed in amounts sufficient in a use solution in an amount of at least about 0.1 wt-% to about 10 wt-%, preferably at least about 0.1 wt-% to about 5 wt-%, more preferably from about 0.1 wt-% to about 1 wt-%.

Catalase and Peroxidase Enzyme

In an aspect of the invention, a catalase or peroxidase enzyme can be used to reduce and/or eliminate the concentration of hydrogen peroxide in an antimicrobial peracid composition. The enzymes catalyze the decomposition of hydrogen peroxide to water and oxygen.

Various sources of catalase enzymes may be employed according to the invention, including: animal sources such as bovine catalase isolated from beef livers; fungal catalases isolated from fungi including *Penicillium chrysogenum*, *Penicillium notatum*, and *Aspergillus niger*; plant sources; bacterial sources such as *Staphylococcus aureus*, and genetic variations and modifications thereof. In an aspect of the invention, fungal catalases are utilized to reduce the hydrogen peroxide content of a peracid composition. Catalases are commercially available in various forms, including liquid and spray dried forms. Commercially available catalase includes both the active enzyme as well as additional ingredients to enhance the stability of the enzyme. Some exemplary commercially available catalase enzymes include Genencor CA-100 and CA-400, as well as Mitsubishi Gas and Chemical (MGC) ASC super G and ASC super 200, and Optimase CA 400L from Genecor International. Additional description of suitable catalase enzymes are disclosed and herein incorporated by reference in its entirety from U.S. Patent Publication No. 2009/0269324.

In an aspect of the invention, catalase enzymes have a high ability to decompose hydrogen peroxide. Beneficially, the reduction or elimination of hydrogen peroxide from oxidizing compositions obviates the various detriments caused by oxidizing agents. In particular, the use of catalase with the peracids compositions provides enhanced antimicrobial benefits without causing the damage associated with conventional oxidizing agents (e.g. peracetic acid, hypochlorite or hypochlorous acid, and/or chlorine dioxide), such as corrosion.

Peroxidase enzymes may also be employed to decompose hydrogen peroxide from a peracid composition. Although peroxidase enzymes primarily function to enable oxidation of substrates by hydrogen peroxide, they are also suitable for effectively lowering hydrogen peroxide to peracid ratios in compositions. Various sources of peroxidase enzymes may be employed according to the invention, including for example animal sources, fungal peroxidases, and genetic variations and modifications thereof. Peroxidases are commercially available in various forms, including liquid and spray dried forms. Commercially available peroxidases include both the active enzyme as well as additional ingredients to enhance the stability of the enzyme.

In some embodiments, the catalase or peroxidase enzyme is able to degrade at least about 50% of the initial concentration of hydrogen peroxide in a peracid composition. Preferably, the enzyme is provided in sufficient amount to reduce the hydrogen peroxide concentration of a peracid composition by at least more than about 50%, more preferably at least about 60%, at least about 70%, at least about 80%, at least about 90%. In some embodiments, the enzyme reduces the hydrogen peroxide concentration of a peracid composition by more than 90%.

In an aspect of the invention, the enzymes are suitable for use and have a tolerance to a wide range of temperatures, including the temperatures ranges in water treatment applications which may range from about 0-80° C. A suitable catalase enzyme will maintain at least 50% of its activity under such storage and/or application temperatures for at least about 10 minutes, preferably for at least about 1 hour.

In an aspect of the invention, a catalase or peroxidase enzyme is present in a use solution of the peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the enzymes will vary depending upon the amount of time within which 50% of the hydrogen peroxide from the peracid composition is removed. In certain aspects of the invention, a catalase or peroxidase enzyme is present in a use solution composition including the water source to be treated in amounts between about 1 ppm and about 1,000 ppm, preferably between about 5 ppm and 500 ppm, and more preferably between about 10 ppm and about 100 ppm.

Defoaming Agents

In an aspect of the invention, a defoaming agent, which can include surfactants and polymers can be used to reduce and/or eliminate foaming in the cleaning of the surfaces disclosed according to the invention. Examples of defoaming agents include, but are not limited to: ethylene oxide/propylene block copolymers such as those available under the name Pluronic N-3; silicone compounds such as silica dispersed in polydimethylsiloxane, polydimethylsiloxane, and functionalized polydimethylsiloxane such as those available under the name Abil B9952; fatty amides, hydrocarbon waxes, fatty acids, fatty esters, fatty alcohols, fatty acid soaps, ethoxylates, mineral oils, polyethylene glycol esters, and alkyl phosphate esters such as monostearyl phosphate. A discussion of defoaming agents may be found, for example, in U.S. Pat. No. 3,048,548 to Martin et al., U.S. Pat. No. 3,334,147 to Brunelle et al., and U.S. Pat. No. 3,442,242 to Rue et al., the disclosures of which are incorporated herein by reference.

In an aspect, various polymers are suitable for use as defoaming agents, including for example polyoxyethylene-polyoxypropylene block copolymer. Particularly preferred defoaming agents include nonionic block copolymers having the general structure: polyoxypropylene core with polyoxyethylene caps Defoaming agents can include surfactants and polymers employed in amounts sufficient in a use solution in an amount of at least about 0.01 wt-% to about 30 wt-%, preferably at least about 0.1 wt-% to about 20 wt-%, more preferably from about 0.1 wt-% to about 10 wt-%.

Surfactants

The surfactants described hereinabove can be used singly or in combination with the methods of the present invention.

In particular, the nonionics and anionics can be used in combination. The semi-polar nonionic, cationic, amphoteric and zwitterionic surfactants can be employed in combination with nonionics or anionics. The above examples are merely specific illustrations of the numerous surfactants which can find application within the scope of this invention. It should be understood that the selection of particular surfactants or combinations of surfactants can be based on a number of factors including compatibility with the membrane at the intended use concentration and the intended environmental conditions including temperature and pH. Accordingly, one should understand that surfactants that may damage a particular membrane during conditions of use should not be used with that membrane. It is expected that the same surfactant, however, may be useful with other types of membranes. In addition, the level and degree of foaming under the conditions of use and in subsequent recovery of the composition can be a factor for selecting particular surfactants and mixtures of surfactants. For example, in certain applications it may be desirable to minimize foaming and, as a result, one would select a surfactant or mixture of surfactants that provides reduced foaming. In addition, it may be desirable to select a surfactant or a mixture of surfactants that exhibits a foam that breaks down relatively quickly so that the composition can be recovered and reused with an acceptable amount of down time. In addition, the surfactant or mixture of surfactants can be selected depending upon the particular soil that is to be removed.

It should be understood that the compositions for use with the methods of the present invention need not include a surfactant or a surfactant mixture, and can include other components. In addition, the compositions can include a surfactant or surfactant mixture in combination with other components. Exemplary additional components that can be provided within the compositions include builders, water conditioning agents, non-aqueous components, adjuvants, carriers, processing aids, enzymes, and pH adjusting agents. When surfactants are included in the peroxyformic acid compositions in a use solution they can be included in an amount of at least about 0.1 wt. % to about 10 wt. %.

Anionic Surfactants

The peroxyformic acid compositions can contain a surfactant component(s) that includes a detersive amount of an anionic surfactant or a mixture of anionic surfactants. Anionic surfactants are desirable in cleaning compositions because of their wetting, detersive properties, and often times good compatibility with membranes. The anionic surfactants that can be used according to the invention include any anionic surfactant available in the cleaning industry. Suitable groups of anionic surfactants include sulfonates and sulfates. Suitable surfactants that can be provided in the anionic surfactant component include alkyl aryl sulfonates, secondary alkane sulfonates, alkyl methyl ester sulfonates, alpha olefin sulfonates, alkyl ether sulfates, alkyl sulfates, and alcohol sulfates. Suitable alkyl aryl sulfonates that can be used in the cleaning composition can have an alkyl group that contains 6 to 24 carbon atoms and the aryl group can be at least one of benzene, toluene, and xylene. A suitable alkyl aryl sulfonate includes linear alkyl benzene sulfonate. A suitable linear alkyl benzene sulfonate includes linear dodecyl benzyl sulfonate that can be provided as an acid that is neutralized to form the sulfonate. Additional suitable alkyl aryl sulfonates include xylene sulfonate and cumene sulfonate. Suitable alkane sulfonates that can be used in the cleaning composition can have an alkane group having 6 to 24 carbon atoms. Suitable alkane sulfonates that can be used include secondary alkane sulfonates. A suitable secondary alkane sulfonate includes sodium C14-C17 secondary alkyl sulfonate. Suitable alkyl methyl ester sulfonates that can be used in the cleaning composition include those having an alkyl group containing 6 to 24 carbon atoms. Suitable alpha olefin sulfonates that can be used in the cleaning composition include those having alpha olefin groups containing 6 to 24 carbon atoms. Suitable alkyl ether sulfates that can be used in the cleaning composition include those having between about 1 and about 10 repeating alkoxy groups, between about 1 and about 5 repeating alkoxy groups. In general, the alkoxy group will contain between about 2 and about 4 carbon atoms. A suitable alkoxy group is ethoxy. A suitable alkyl ether sulfate is sodium lauryl ether ethoxylate sulfate. Suitable alkyl sulfates that can be used in the cleaning composition include those having an alkyl group containing 6 to 24 carbon atoms. Suitable alkyl sulfates include, but are not limited to, sodium lauryl sulfate and sodium lauryl/myristyl sulfate. Suitable alcohol sulfates that can be used in the cleaning composition include those having an alcohol group containing about 6 to about 24 carbon atoms.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678. The disclosures of the above references relating to anionic surfactants are incorporated herein by reference.

Nonionic Surfactants

The peroxyformic acid compositions can contain a surfactant component(s) that includes a detersive amount of an nonionic surfactant or a mixture of nonionic surfactants. Nonionic surfactants can be included in the composition to enhance soil removal properties. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polyhydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water-soluble compound having the desired degree of balance between hydrophilic and hydrophobic properties.

Nonionic surfactants that can be used in the composition include polyalkylene oxide surfactants (also known as polyoxyalkylene surfactants or polyalkylene glycol surfactants). Suitable polyalkylene oxide surfactants include polyoxypropylene surfactants and polyoxyethylene glycol surfactants. Suitable surfactants of this type are synthetic organic polyoxypropylene (PO)-polyoxyethylene (EO) block copolymers. These surfactants include a di-block polymer comprising an EO block and a PO block, a center block of polyoxypropylene units (PO), and having blocks of polyoxyethylene grafted onto the polyoxypropylene unit or a center block of EO with attached PO blocks. Further, this surfactant can have further blocks of either polyoxyethylene or polyoxypropylene in the molecules. A suitable average molecular weight range of useful surfactants can be about 1,000 to about 40,000 and the weight percent content of ethylene oxide can be about 10-80 wt. %.

Additional nonionic surfactants include alcohol alkoxylates. An suitable alcohol alkoxylate include linear alcohol ethoxylates. Additional alcohol alkoxylates include alkylphenol ethoxylates, branched alcohol ethoxylates, secondary alcohol ethoxylates, castor oil ethoxylates, alkylamine ethoxylates, tallow amine ethoxylates, fatty acid ethoxylates, sorbital oleate ethoxylates, end-capped ethoxylates, or mixtures thereof. Additional nonionic surfactants include amides such as fatty alkanolamides, alkyldiethanolamides, coconut diethanolamide, lauramide diethanolamide, cocoamide diethanolamide, polyethylene glycol cocoamide, oleic diethanolamide, or mixtures thereof. Additional suitable nonionic surfactants include polyalkoxylated aliphatic base, polyalkoxylated amide, glycol esters, glycerol esters, amine oxides, phosphate esters, alcohol phosphate, fatty triglycerides, fatty triglyceride esters, alkyl ether phosphate, alkyl esters, alkyl phenol ethoxylate phosphate esters, alkyl polysaccharides, block copolymers, alkyl glucosides, or mixtures thereof.

Other exemplary nonionic surfactants for use with the methods of the present invention are disclosed in the treatise Nonionic Surfactants, edited by Schick, M. J., Vol. 1 of the Surfactant Science Series, Marcel Dekker, Inc., New York, 1983, the contents of which is incorporated by reference herein. A typical listing of nonionic classes, and species of these surfactants, is also given in U.S. Pat. No. 3,929,678. Further examples are given in "Surface Active Agents and Detergents" (Vol. I and II by Schwartz, Perry and Berch). The disclosures of these references relating to nonionic surfactants are incorporated herein by reference.

Amphoteric Surfactants

Amphoteric surfactants can also be used to provide desired detersive properties. Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge. Suitable amphoteric surfactants include, but are not limited to: sultaines, amphopropionates, amphodipropionates, aminopropionates, aminodipropionates, amphoacetates, amphodiacetates, and amphohydroxypropylsulfonates.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Zwitterionic Surfactants

In some embodiments, zwitterionic surfactants are used with the methods of the invention. Zwitterionic surfactants can be thought of as a subset of the amphoteric surfactants. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A typical listing of zwitterionic classes, and species of these surfactants, is given in U.S. Pat. No. 3,929,678. Further examples are given in "Surface Active Agents and Detergents" (Vol. I and II by Schwartz, Perry and Berch). The disclosures of zwitterionic surfactants in the above references are incorporated herein by reference.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following Examples are provided herein:

Various commercially-available stock solutions were employed in formulations (available from various sources) including: methane sulfonic acid (70%), linear alkylbenzene sulphonates (96%), sodium xylene sulfonate (40%), formic acid (85%), and hydrogen peroxide (50%).

POAA: a commercial product containing 5.25 to 6.4% peroxyacetic acid and 25.6 to 29.4% $H_2O_2$.

Exemplary peroxyformic acid compositions generated in situ and employed in some of the Examples are listed in the Table 1 below:

TABLE 1

| Component | PFA-30-1 (wt %) | PFA-30-2 (wt %) | 30-3 (wt %) |
|---|---|---|---|
| Water | 0.00 | 0.00 | 16.25 |
| MSA (70%) | 3.0 | 3.0 | 3.0 |
| LAS (96%) | 4.93 | 0 | 4.93 |

TABLE 1-continued

| Component | PFA-30-1 (wt %) | PFA-30-2 (wt %) | 30-3 (wt %) |
|---|---|---|---|
| Formic acid (85%) | 75.82 | 80.75 | 75.82 |
| $H_2O_2$ (50%) | 16.25 | 16.25 | 0 |
| Total | 100.00 | 100.00 | 100.00 |
| PFA (5 min after mixing) | 10.19% | 9.22% | 0.00% |

The peroxyformic acid compositions shown in Table 1 were made from a two part system. Part A provided the formic acid and optionally with other ingredients excluding the $H_2O_2$. Part B for the formulations PFA 30-1 and PFA 30-2 provided $H_2O_2$ and optionally with other ingredients excluding the formic acid provided in Part A. On mixing Part A and Part B under ambient conditions, peroxyformic acid (PFA) reached maximum level within 5 min., i.e. the compositions were ready to use. Composition 30-3 is a formic acid composition and not a peroxyformic acid composition.

Accordingly, the peroxyformic acid formed provides a superior biocide against microorganisms, especially spores and biofilms suitable for the uses disclosed herein according to the embodiments of the invention.

Example 1

The removal of biofilm was tested to determine efficacy of biofilm removal and kill rates of *Pseudomonas aeruginosa*. *Pseudomonas* are well-known as common 'pioneer' bacteria and often tested for biofilm-inhibiting agents' effectivity. The bacteria are known to excrete polysaccharides and generate biofilm on a variety of surfaces very rapidly (including, for example, membrane filtration elements), as well as commonly demonstrate resistance to various antimicrobial compositions. However, bacteria that exist in a biofilm are phenotypically different from suspended cells of the same genotype; therefore the study of biofilm in the laboratory requires protocols that account for this difference. Laboratory biofilms are engineered in growth reactors designed to produce a specific biofilm type. Altering system parameters correspondingly results in a change in the biofilm.

*Pseudomonas aeruginosa* (ATCC 700888) was the organism used. An isolated colony was aseptically removed from an R2A plate and placed into 100 ml of sterile bacterial liquid growth broth (300 mg/L) and incubated in an environmental shaker at 35° C. for 20-24 hours. Viable bacterial density should equal 108 CFU/ml, and may be checked by serial dilution and plating. *Pseudomonas aeruginosa* were grown in a CDC reactor system for 48 hours at room temperature. See Goeres, D. M., et al., Statistical assessment of a laboratory method for growing biofilms, Microbiology 151:757-762 (2005). Biofilm challenge is approximately 8 logs throughout testing from a 48 hour growth.

Biofilms were prepared on membrane surfaces for evaluation. Small Koch HFK-131 UF membrane rectangles were prepared by punching out a spiral wound membrane and placing the membrane disk into a plastic rectangle used to serve as "framing material". The membranes were placed into the CDC rod and used for testing. After the biofilm was developed, the membrane rectangles were removed and placed into a sterile plastic centrifuge tube. Each exemplary composition was pipette into the centrifuge tube in duplicate and exposed to the membrane rectangles for the specified exposure time (5 or 10 minutes) at room temperature. After the specified exposure time the solutions were neutralized in Neutralizer Broth, vortexed, sonicated, serially diluted and plated for plate counts. The average log reduction for each evaluated composition was obtained as follows: peroxyformic acid (Formulations 30-1 and 30-2), untreated control not containing peroxyformic acid (Formulation 30-3), and a known antimicrobial composition (Oxonia Active). The results of these experiments are shown in FIG. 1.

As can be seen in FIG. 1, all three exemplary compositions efficiently reduced *Pseudomonas aeruginosa* biofilm at the indicated exposure times. Compositions 30-1 and 30-2 at the concentration of 0.3% (product) provide significant log reduction in (>6.68) at both the 5 and 10 minute exposure times, while the average log reduction for composition 30-3 containing formic acid alone (4.15 at 5 minutes and 3.02 at 10 minutes) has significantly less efficacy against the test microorganism. At least a 3 log reduction in the biofilm organisms is conventionally required as a commercial threshold for biofilm treatments to comply with EPA requirements. Accordingly, the PFA compositions according to the invention provide suitable compositions for biofilm treatment. Accordingly, the peroxyformic acid formed provides a superior biocide against microorganisms, especially spores and biofilms suitable for the uses disclosed herein according to the embodiments of the invention.

Example 2

Mesophilic bacterial endospores (also referred to as spores in this Example) were further evaluated for the efficacy of peroxyformic acid or removal and kill rates. The procedure outlined in Example 1 was followed replacing *Pseudomonas aeruginosa* with field isolates of mesophilic spores against varying concentrations of actives of the peroxyformic acid according to a lower active concentration (0.15% PFA composition 30-1 and 0.2% PFA composition 30-1) at a 5 minute exposure time and compared to peroxyacetic acid compositions (0.2% or 0.25% of peracetic acid compositions). The results of these experiments are shown in FIG. 2.

Figure 2:
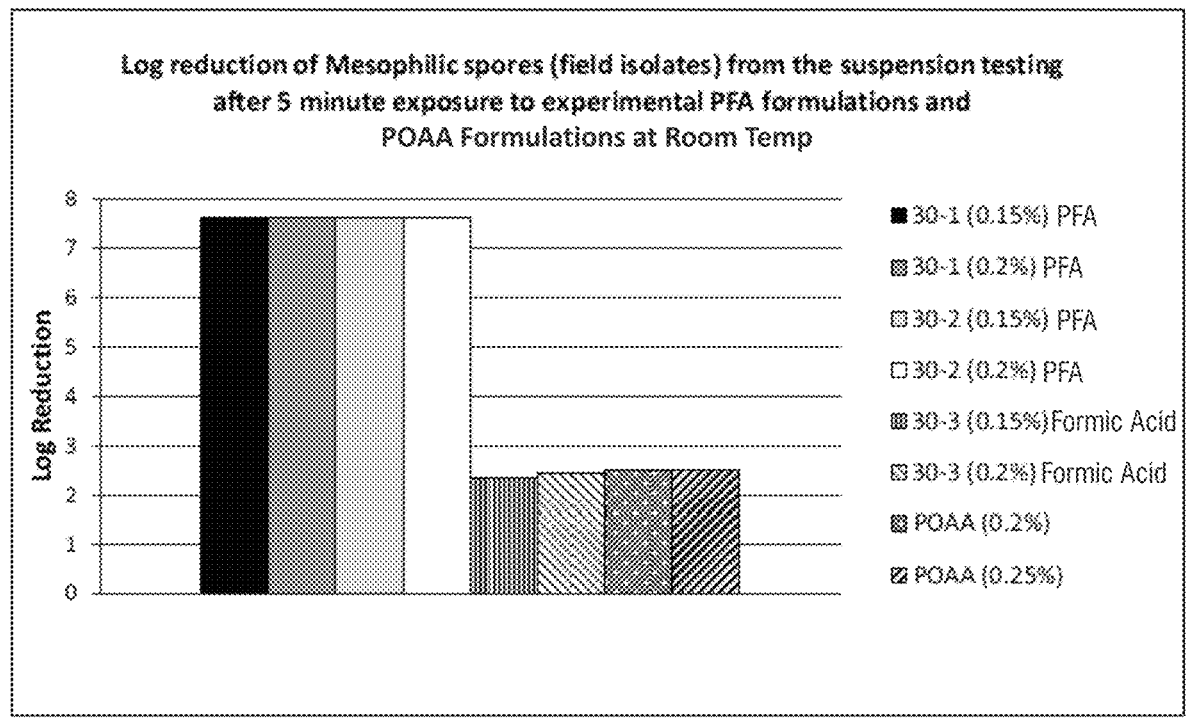
FIG. 2 shows the average log reduction of mesophilic spores after exposure to the peroxyformic acid formulations according to an embodiment of the invention.

As illustrated in FIG. 2, both concentrations (0.15% and 0.2%) of formulas 30-1 and 30-2 were particularly effective in reducing mesophilic spores at a 5 minute exposure time at a lower actives concentration than what was evaluated in Example 1. Composition 30-3 (0.15% and 0.2%) showed comparable log reduction with peracetic acid composition.

Example 3

Figure 3:
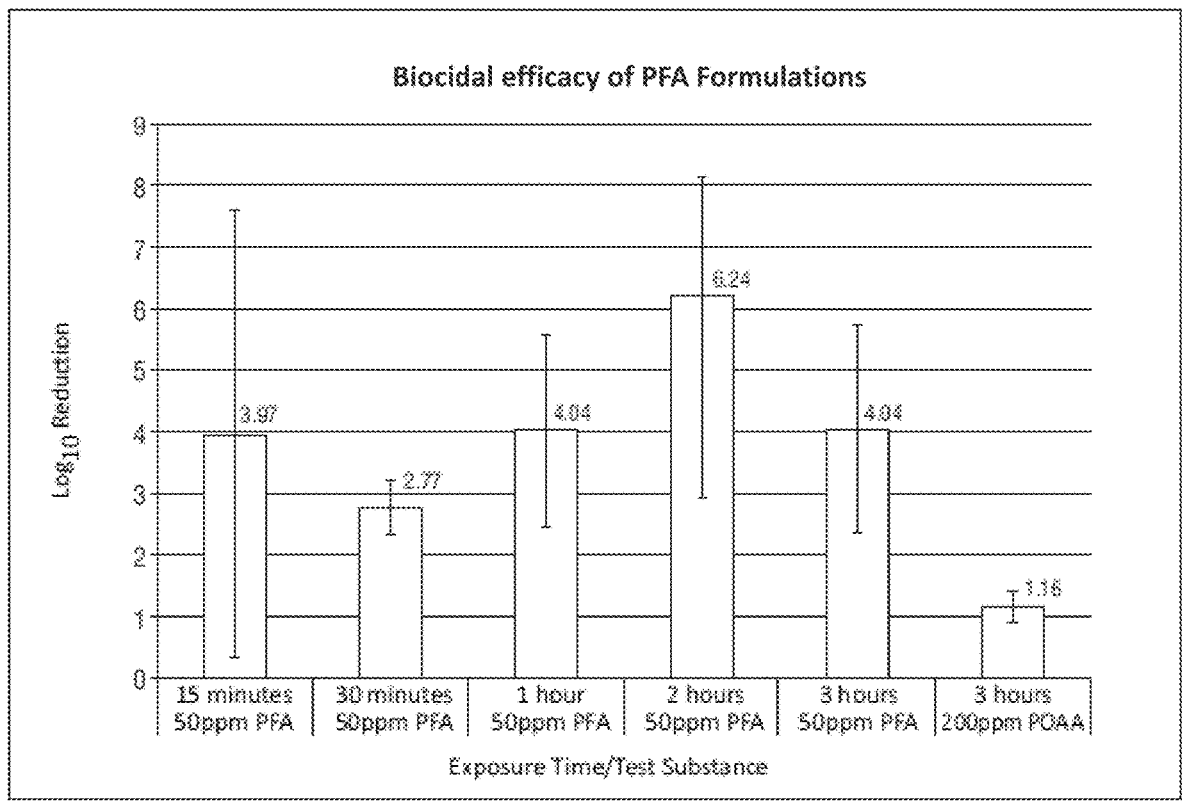
FIG. 3 shows the beneficial performance of peroxyformic acid in anti-biofilm efficacy with shorter exposure time and lower concentrations than POAA.

Reduction of *P. aeruginosa* Biofilm Using Different Exposure Times of Peroxyformic Acid. *P. aeruginosa* ATCC 15442 biofilm was grown on the surface of 24 polycarbonate coupons following ASTM method E2562-12: Standard Test Method for Quantification of *Pseudomonas aeruginosa* Biofilm Grown with High Shear and Continuous Flow using CDC Biofilm Reactor. After 48 hours of biofilm establishment, the coupons were removed from the reactor and placed into individual centrifuge tubes. Three coupons per test condition were tested for disinfectant efficacy using ASTM method E2871-12: Standard Test Method for Evaluating Disinfectant Efficacy against *Pseudomonas aeruginosa* Biofilm Grown in CDC Biofilm Reactor using Single Tube Method. Sets of three coupons were exposed to 4 mL of 50 ppm PFA for exposure times of 15 minutes, 30 minutes, 1 hour, 2 hours and 3 hours, while coupons treated with 200 ppm POAA were exposed for 3 hours only. After the desired exposure time, 16 mL of neutralizing medium was added on top of the chemistry to inactive antimicrobial performance. This was followed with a series of vortexing and sonicating steps to remove any biofilm from the coupon surface into the solution for plating and enumeration. As shown in FIG. 3, peroxyformic acid achieves greater anti-biofilm efficacy with shorter exposure time and lower concentrations than POAA.

Example 4

Additional biocidal performance of performic acid was evaluated for log reduction of *Pseudomonas aeruginosa* as shown in Table 2.

TABLE 2

| Test Systems: | *Pseudomonas aeruginosa* ATCC 15442 |
|---|---|
| Test Substance Diluents: | 500 ppm synthetic hard water, pH 7.74 |
| Test Substances: | A. 0.5 ppm PFA: 47 µL PFA Concentrate (0.107% PFA)/99 mL diluent pH 6.71 |
| | B. 1.0 ppm PFA: 93 µL PFA Concentrate (0.107% PFA)/99 mL diluent pH 6.31 |
| | C. 2.0 ppm PFA: 185 µL PFA Concentrate (0.107% PFA)/99 mL diluent pH 5.34 |
| Exposure Time(s): | 10 minutes and 4 hours |
| Neutralizer: | 9 mL DE Broth |
| Test Temperature | 25° C. |
| Plating Medium: | TGE |
| Incubation: | 35° C. for 48 hours |

Figure 4:
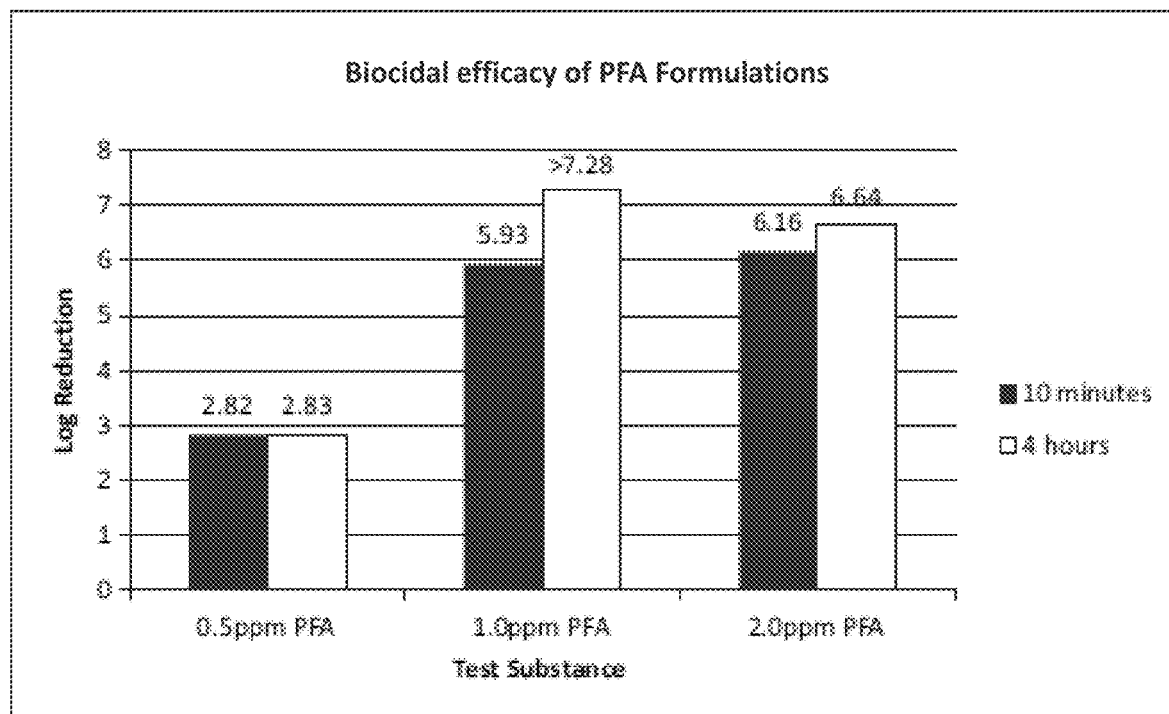
FIG. 4 shows the results of biocidal efficacy of performic acid generated in situ according to embodiments of the invention.

FIG. 4 shows the results of biocidal efficacy after 10 minutes contact and 4 hours contact showing the beneficially efficacy of performic acid generated in situ according to the invention at varying concentrations.

Example 5

Figure 5:
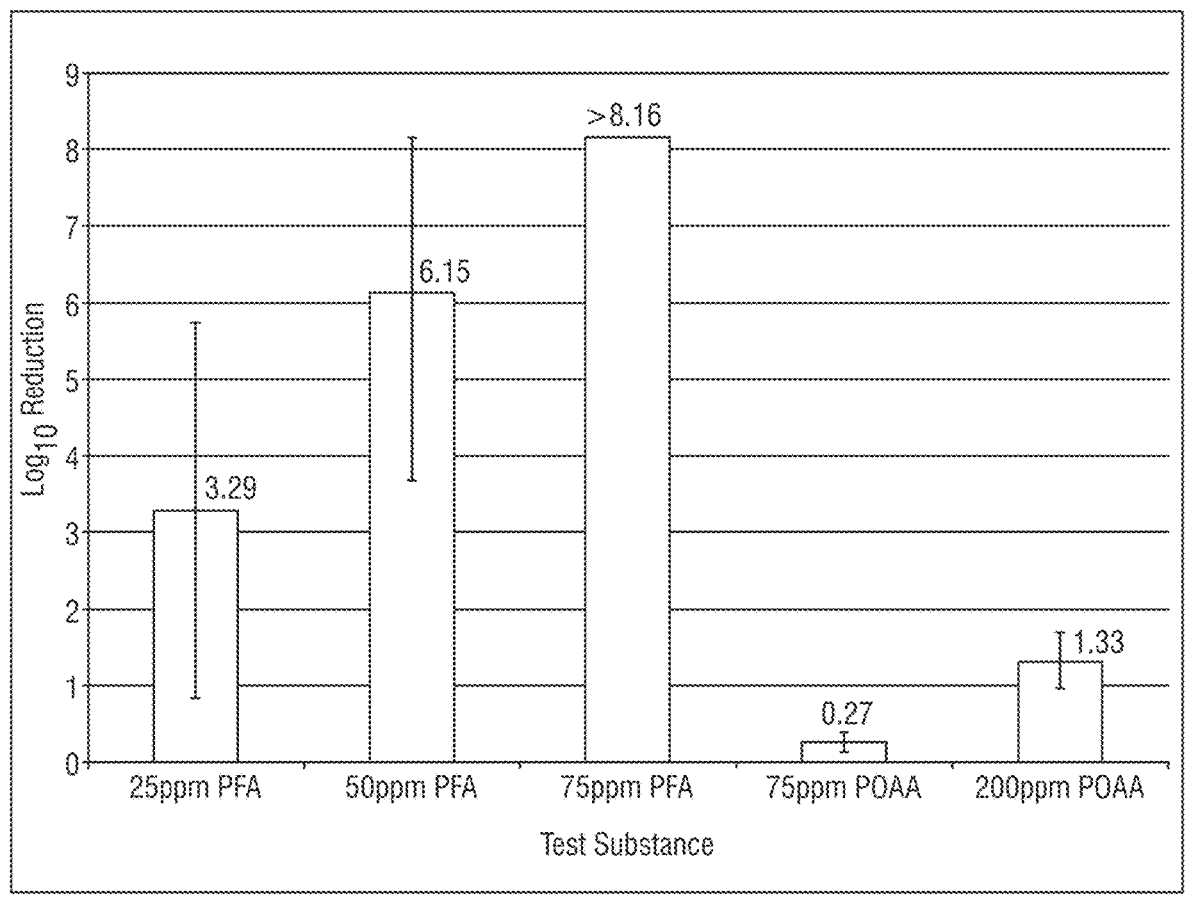
FIGS. 5-6 show the results of biocidal efficacy of performic acid compared to peroxyacetic acid according to embodiments of the invention.
Figure 6:
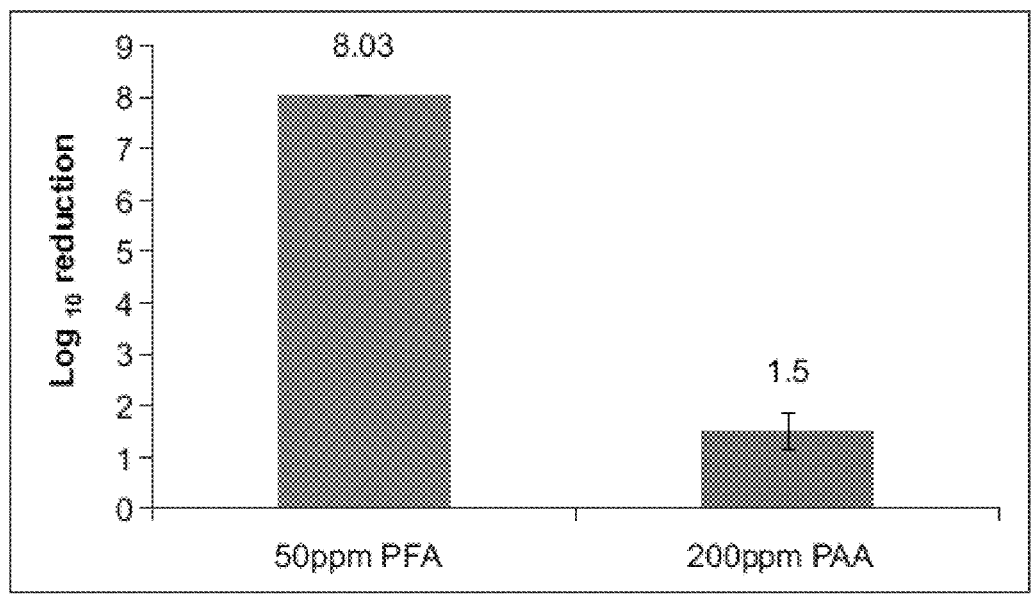

Additional biocidal performance of performic acid was evaluated for log reduction of *Pseudomonas aeruginosa* in comparison to another peroxyacid. A *Pseudomonas* biofilm was treated with 50 ppm active of PFA and compared to efficacy treated with 200 ppm PAA. *Pseudomonas* biofilms were grown in a CDC biofilm reactor on a poly carbonate coupons. Appropriate concentration of the treatment substance were diluted in hard water at pH 7.71 diluent. Test chemicals were exposed for 3 hrs after which they were treated with 16 mLs of thiosulfate to neutralize any oxidants. The untreated control and treated *Pseudomonas* were plated on a TGE media and incubated at 35° C. for 48 hrs. A 4 hr reduction was monitored by colony counting of *Pseudomonas* on plates. Results are shown in FIG. 5 demonstrating the beneficially efficacy of PFA generated according to the invention. Further testing of the log reduction between decreased concentration of the actives of performic acid in comparison to peracetic acid is shown in FIG. 6 demonstrating the substantially increased reduction in *Pseudomonas aeruginosa* in comparison to a substantially higher concentration of another peroxyacid.

Example 6

Removal and/or prevention of biofilm fouling of $CO_2$ scrubbers was tested with peroxyformic acid. Such scrubbers were evaluated in an ethanol fermentation plant which conventionally employs CIP cleaning process with hot caustic recirculated through the system every few weeks to clean any biofilm which has accumulated since the prior CIP cleaning cycle. This problem to be solved is the prevention of biofilm in the systems instead of removal of the biofilm after the same has been formed. The prevention of biofilm is more desirable than removal, as biofilm scuffs off and undesirably plugs lines within the system and in an fermentation facility the stream of reclaimed ethanol that goes back into the process may undesirably carry microbes from the biofilm. As a result, the use of performic acid was compared to the conventional CIP cleaning for efficacy.

In an exemplary treatment cycle the following conditions were employed:

Bisulfite pump cycled off;
5 minute rinse of scrubber columns with water;
Inject peroxyformic acid (PFA) for 30 minute PFA treatment at 75-100 ppm PFA at ambient temperature and at 80 gallons per minute flow (approximately 12 L/cycle treatment)—rates and intervals can vary depending on system and desired cleaning frequency;
PFA supply stops;
Restart bisulfite pump; and
Restart processing of system and rerun cycle at a predetermined amount of time (such as from as often as 3-4 hours, to weekly treatments).

According to such an exemplary embodiment, an onsite PFA generator can be employed for generating the chemistry at a point of use. In such an embodiment for dosing directly into the scrubber columns, either formic acid or water may be employed for clearing the dosing line after the PFA is generated. In such an embodiment it is desired to employ a controller to time the dosing of the PFA, formic acid (and/or other reagents employed in a generator to provide the PFA), water and bisulfite.

According to such an exemplary embodiment, it may be desired to further employ a solution to neutralize or over ride the bisulfite. In an alternative embodiment, the bisulfite can be discontinued (or shut off) instead of counteracting the oxidizing chemistry, according to the preference of a user and system.

Beneficially, the use of peroxyformic acid in the $CO_2$ scrubbers allowed for extended runs of the system without shutdown (for CIP cleaning), biofilm did not form, scrubber efficiency increased as measured by flow, and biofilm did not reenter the upstream processes in the plant. $CO_2$ flow, during PFA cycles does not reduce the efficacy of treatment compared to alkaline treatments due to the $CO_2$ acting to reduce the alkalinity of sodium hydroxide and other caustic cleaners to bicarbonate and or carbonate in turn reducing the effectiveness of cleaning. Since PFA is an acidic application, this neutralization or acidification from the $CO_2$ flow is no longer an issue. The use of an onsite peroxyformic acid generator provided enhanced convenience and user-directed generation of the peracid.

While this invention may be embodied in many different forms, there are described scientific papers, and any other referenced materials mentioned herein are incorporated by reference in their entirety. Furthermore, the invention encompasses any possible combination of some or all of the various embodiments mentioned herein, described herein and/or incorporated herein. In addition the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

What is claimed is:

1. A method for removing microorganisms on an industrial processing hard surface comprising:
   contacting the hard surface with a peroxyformic acid composition comprising at least about 25 ppm peroxyformic acid, wherein the composition is dosed on site and generated in situ; and
   removing biofilm and microbial growth from the hard surface,
   wherein the surface is a scrubber and/or cooling tower, tower packing materials contained in the scrubber and/or cooling tower, drain, sump, or floor.

2. The method of claim 1, wherein the surface is a $CO_2$ scrubber in a fermentation system, wherein the scrubber contains packing materials, and wherein the scrubber surface and packing material surface is contacted with the peroxyformic acid composition in an intermittent treatment of a process water stream feeding the scrubber.

3. The method of claim 1, wherein the removing of microbial growth from the scrubber surface prevents plugging and fouling, and enhances flow, and/or prevents biofilm formation and fouling, and wherein the treatment with the peroxyformic acid composition does not negatively impact the surface being treated and does not result in residual peracid in effluent from the system.

4. The method of claim 1, wherein the treatment with the peroxyformic acid composition does not contaminate any by-products from the system.

5. The method of claim 1, further comprising: a pre-rinse or flushing step of washing the surface with water, an alkaline and/or acidic solution, a step of stopping any flow of a bisulfate source (or other cleaning agent) from contacting the surface, and/or a step of treating the surface in combination with the peroxyformic acid, before the peroxyformic acid, and/or after the peroxyformic acid, with one or more of the following agents: a defoaming composition, an additional sanitizing agent, an oxidant, and/or a neutralizing composition for any $CO_2$ on the surface.

6. The method of claim 1, further comprising additional treatment cycles comprising an acidic treatment, an enzymatic treatment, an alkaline treatment and/or a neutral treatment either before or after the peroxyformic acid composition contacts the surface.

7. The method of claim 1, wherein the surface in need of treatment is contacted with from about 0.0075% to about 0.1% active peroxyformic acid.

8. The method of claim 1, wherein the surface is contacted with peroxyformic acid for at least 60 seconds to about 30 minutes.

9. The method of claim 1, wherein the surface is contacted with peroxyformic acid on a frequency of at least once per week.

10. The method of claim 1, wherein the surface is contacted with the peroxyformic acid composition at a temperature from about 2° C. to 60° C.

11. The method of claim 1, wherein the peroxyformic acid composition is generated in situ by contacting formic acid with hydrogen peroxide, wherein before said contacting, the ratio between the concentration of said formic acid (w/v) and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher within about 1 hour of said contacting.

12. The method of claim 11, wherein before the contacting, the formic acid is provided in a composition that comprises formic acid or a substance that generates formic acid upon contact with an aqueous composition, and the hydrogen peroxide is provided in a composition that comprises hydrogen peroxide or a substance that generates hydrogen peroxide upon contact with an aqueous composition.

13. The method of claim 11, wherein at least about 1% peroxyformic acid is formed in the aqueous composition within about 5 minutes of the contacting.

14. The method of claim 13, wherein the contacting of the reagents to form peroxyformic acid is conducted in the presence of a mineral acid catalyst, an acidulant and/or an enzyme.

15. The method of claim 11, wherein the peroxyformic acid composition comprises at least one additional agent selected from the group consisting of a stabilizing agent, a wetting agent, a surfactant, and a defoamer.

16. A method for removing microbial growth and mineral deposits on an industrial processing system surface comprising:
   turning off a chemical supply to the industrial processing system;
   contacting the surface with at least about 25 ppm peroxyformic acid composition generated in situ; and
   removing biofilm and microorganisms mineral deposits on the membrane,
   wherein the industrial processing system surface is a scrubber and/or cooling tower, tower packing materials contained in the scrubber and/or cooling tower, drain, sump, or floor.

17. The method of claim 16, wherein the surface is $CO_2$ scrubber in a fermentation system, and wherein the scrubber surface is contacted with the peroxyformic acid composition in an intermittent treatment of a process water stream feeding the scrubber.

18. The method of claim 16, further comprising a step of stopping any flow of a bisulfate source (or other cleaning agent) from contacting the surface, and/or a step of treating the surface in combination with the peroxyformic acid, before the peroxyformic acid, and/or after the peroxyformic acid, with one or more of the following agents: a defoaming composition, an additional sanitizing agent, an oxidant, and/or a neutralizing composition for any $CO_2$ on the surface.

\* \* \* \* \*